(12) United States Patent
Hanley-Bowdoin et al.

(10) Patent No.: US 6,800,793 B2
(45) Date of Patent: Oct. 5, 2004

(54) GEMINIVIRUS RESISTANT TRANSGENIC PLANTS

(75) Inventors: Linda Hanley-Bowdoin, Raleigh, NC (US); Beverly M. Orozco, Raleigh, NC (US); Ling-Jie Kong, Raleigh, NC (US); Wilhelm Gruissem, Berkeley, CA (US)

(73) Assignees: North Carolina State University, Raleigh, NC (US); Regents of the University of California, Oakland, CA (US)

(*) Notice: Subject to any disclaimer, the term of this patent is extended or adjusted under 35 U.S.C. 154(b) by 0 days.

(21) Appl. No.: 09/289,346

(22) Filed: Apr. 9, 1999

(65) Prior Publication Data

US 2002/0138867 A1 Sep. 26, 2002

Related U.S. Application Data

(60) Provisional application No. 60/125,004, filed on Mar. 18, 1999.

(51) Int. Cl.[7] .................. C12N 15/74; C12N 15/11; A01H 11/00; A01H 5/00
(52) U.S. Cl. ............. 800/279; 800/295; 800/317.2; 800/301; 536/23.1; 435/320.1
(58) Field of Search .................. 800/279, 295, 800/278; 536/23.72, 24.1; 435/69.1, 410, 419, 235; 530/350

(56) References Cited

U.S. PATENT DOCUMENTS 5,850,023 A  12/1998  Elmer et al. ............ 800/205

FOREIGN PATENT DOCUMENTS

| WO | WO 97/39110 | 10/1997 |
|---|---|---|
| WO | WO 97/42315 | 11/1997 |
| WO | WO 97/42316 | 11/1997 |

OTHER PUBLICATIONS

Hartl, D. Genetics. 3rd edition (1994) p213. Jones & Bartlett Publishers, Boston.*
Durfee et al (2000) Plant Mol Biol 43:635–642.*
Dahiya et al (2000)Mol Cell Biol 20:6799–6805.*
Picksley SM et al (1994) Curr Op Cell Biol 6:853–858.*
Williams, L et al (2000) Trends in Plant Science vol. 5 No. 6 239–40.*
Gutierrez, C (2000) Plant Mol Biol 43:763–772.*
Ach, R et al (1997) Mol Cell Biol 17:5077–5086.*
Orzoco et al (2000) JBC 275: 6114–6122.*
Noris, E et al (1996) Virology 224: 130–138.*
Hong, Yiguo, et al., *Virus Resistance in Nicotiana benthamiana Conferred by African Cassava Mosaic Virus Replication–Associated Protein (AC1) Transgene*, MPMI, vol. 9, No. 4, pp. 219–225 (May 1996).
Hanson, Stephen F., et al., *Mutational Analysis of a Putative NTP–Binding Domain in the Replication–Associated Protein (AC1) of Bean golden Mosaic Geminivirus*, Virology, vol. 211, No. 1, pp. 1–9 (Aug. 1, 1995).

* cited by examiner

*Primary Examiner*—Phuong T. Bui
*Assistant Examiner*—Georgia L. Helmer
(74) *Attorney, Agent, or Firm*—Myers Bigel Sibley & Sajovec, P.A.

(57) ABSTRACT

Transgenic plants with increased resistance to geminivirus infection, and nucleic acid constructs useful in producing such plants, are described. The transgenic plants express a mutant AL1/C1 geminivirus protein, which increases resistance to infection by at least one geminivirus, compared to a non-transformed control plant.

4 Claims, 7 Drawing Sheets

FIGURE 1

TGMV Rep, amino acids 110-179:
TLVWGEFQVD GRSARGGCQT SNDAAAEALN ASSKEEALQI IREKIPEKYL FQFHNLNSNL DRIFDKTPEP (SEQ ID NO:1)

Ala 1 mutant:
TLVWGEFQVD GAAAAGGCQT SNDAAAEALN ASSKEEALQI IREKIPEKYL FQFHNLNSNL DRIFDKTPEP (SEQ ID NO:2)

Ala4+5 mutant:
TLVWGEFQVD GRSARGGCQT SNDAAAAALA ASSAAAALQI IREKIPEKYL FQFHNLNSNL DRIFDKTPEP (SEQ ID NO:3)

Ala6 mutant:
TLVWGEFQVD GRSARGGCQT SNDAAAEALN ASSKEEALQI IAAAIPEKYL FQFHNLNSNL DRIFDKTPEP (SEQ ID NO:4)

Ala7 mutant:
TLVWGEFQVD GRSARGGCQT SNDAAAEALN ASSKEEALQI IREKIPAAAL FQFHNLNSNL DRIFDKTPEP (SEQ ID NO:5)

Ala8 mutant:
TLVWGEFQVD GRSARGGCQT SNDAAAEALN ASSKEEALQI IREKIPEKYL FAFAALNSNL DRIFDKTPEP (SEQ ID NO:6)

Ala9 mutant:
TLVWGEFQVD GRSARGGCQT SNDAAAEALN ASSKEEALQI IREKIPEKYL FQFHNLNSAL AAIFDKTPEP (SEQ ID NO:7)

Ala13 mutant:
TLVWGEAAVD GRSARGGCQT SNDAAAEALN ASSKEEALQI IREKIPEKYL FQFHNLNSNL DRIFDKTPEP (SEQ ID NO:8)

Ala14 mutant:
TLVWGEFQVA GRSARGGCQT SNDAAAEALN ASSKEEALQI IREKIPEKYL FQFHNLNSNL DRIFDKTPEP (SEQ ID NO:9)

Leu mutant:
TLVWGEFQVD GRSARGGCQT SNDLLLEALN ASSKEEALQI IREKIPEKYL FQFHNLNSNL DRIFDKTPEP (SEQ ID NO:10)

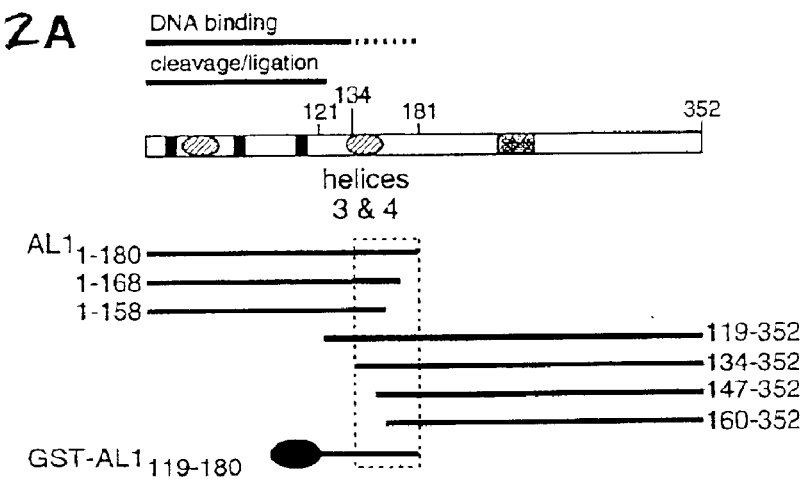
Fig. 2A
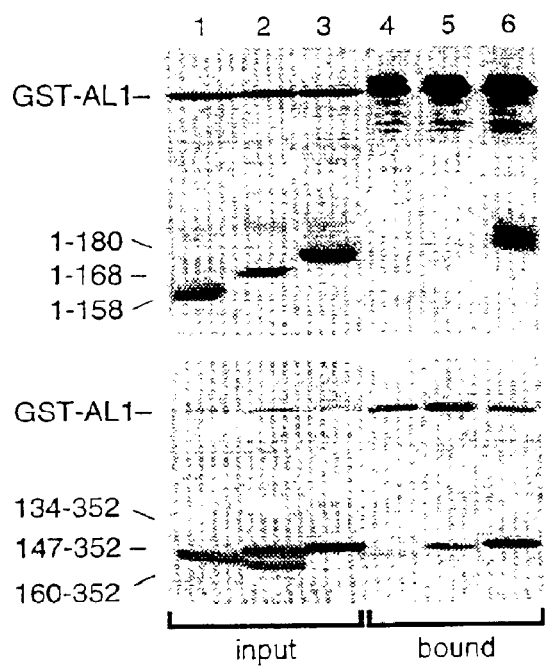
Fig. 2B
Fig. 2C
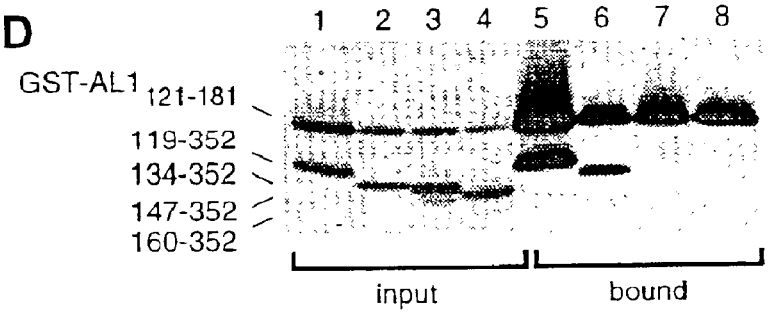
Fig. 2D

SEQUENCE LISTING

```
<160> NUMBER OF SEQ ID NOS: 30

<210> SEQ ID NO 1
<211> LENGTH: 70
<212> TYPE: PRT
<213> ORGANISM: Tomato golden mosaic virus

<400> SEQUENCE: 1

Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70

<210> SEQ ID NO 2
<211> LENGTH: 70
<212> TYPE: PRT
<213> ORGANISM: Tomato golden mosaic virus
<220> FEATURE:
<221> NAME/KEY: MISC_FEATURE
<222> LOCATION: (12)..(15)
<223> OTHER INFORMATION: RS-R125 (Ala1) mutation
```

-continued

```
<400> SEQUENCE: 2

Thr Leu Val Trp Gly Glu Phe Gln Val Asp Gly Ala Ala Ala Ala Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70

<210> SEQ ID NO 3
<211> LENGTH: 70
<212> TYPE: PRT
<213> ORGANISM: Tomato golden mosaic virus
<220> FEATURE:
<221> NAME/KEY: MISC_FEATURE
<222> LOCATION: (27)..(36)
<223> OTHER INFORMATION: E--N140 + KEE146 (Ala4+5) mutation

<400> SEQUENCE: 3

Thr Leu Val Trp Gly Glu Phe Gln Val Asp Gly Arg Ser Ala Arg Gly
1               5                   10                  15

Gly Cys Gln Thr Ser Asn Asp Ala Ala Ala Ala Leu Ala Ala Ser
            20                  25                  30

Ser Ala Ala Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70

<210> SEQ ID NO 4
<211> LENGTH: 70
<212> TYPE: PRT
<213> ORGANISM: Tomato golden mosaic virus
<220> FEATURE:
<221> NAME/KEY: MISC_FEATURE
<222> LOCATION: (42)..(44)
<223> OTHER INFORMATION: REK154 (Ala6) mutation

<400> SEQUENCE: 4

Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Ala Ala Ala Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70

<210> SEQ ID NO 5
<211> LENGTH: 70
<212> TYPE: PRT
<213> ORGANISM: Tomato golden mosaic virus
<220> FEATURE:
<221> NAME/KEY: MISC_FEATURE
<222> LOCATION: (47)..(49)
```

-continued

<223> OTHER INFORMATION: EKY159 (Ala7) mutation

<400> SEQUENCE: 5

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Ala Ala
        35                  40                  45

Ala Leu Phe Gln Phe His Asn Leu Asn Ser Asn Leu Asp Arg Ile Phe
    50                  55                  60

Asp Lys Thr Pro Glu Pro
65                  70
```

<210> SEQ ID NO 6
<211> LENGTH: 70
<212> TYPE: PRT
<213> ORGANISM: Tomato golden mosaic virus
<220> FEATURE:
<221> NAME/KEY: MISC_FEATURE
<222> LOCATION: (52)..(55)
<223> OTHER INFORMATION: Q-HN165 (Ala8) mutation

<400> SEQUENCE: 6

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Ala Phe Ala Ala Leu Asn Ser Asn Leu Asp Arg Ile Phe
    50                  55                  60

Asp Lys Thr Pro Glu Pro
65                  70
```

<210> SEQ ID NO 7
<211> LENGTH: 70
<212> TYPE: PRT
<213> ORGANISM: Tomato golden mosaic virus
<220> FEATURE:
<221> NAME/KEY: MISC_FEATURE
<222> LOCATION: (59)..(62)
<223> OTHER INFORMATION: N-DR172 (Ala9) mutation

<400> SEQUENCE: 7

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Ala Leu Ala Ala Ile Phe
    50                  55                  60

Asp Lys Thr Pro Glu Pro
65                  70
```

<210> SEQ ID NO 8
<211> LENGTH: 70
<212> TYPE: PRT
<213> ORGANISM: Tomato golden mosaic virus
<220> FEATURE:

-continued

<221> NAME/KEY: MISC_FEATURE
<222> LOCATION: (7)..(8)
<223> OTHER INFORMATION: FQ118 (Ala13) mutation

<400> SEQUENCE: 8

Thr Leu Val Trp Gly Glu Ala Ala Val Asp Gly Arg Ser Ala Arg Gly
1 5 10 15

Gly Cys Gln Thr Ser Asn Asp Ala Ala Ala Glu Ala Leu Asn Ala Ser
20 25 30

Ser Lys Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 9
<211> LENGTH: 70
<212> TYPE: PRT
<213> ORGANISM: Tomato golden mosaic virus
<220> FEATURE:
<221> NAME/KEY: MISC_FEATURE
<222> LOCATION: (10)..(10)
<223> OTHER INFORMATION: D120 (Ala14) mutation

<400> SEQUENCE: 9

Thr Leu Val Trp Gly Glu Phe Gln Val Ala Gly Arg Ser Ala Arg Gly
1 5 10 15

Gly Cys Gln Thr Ser Asn Asp Ala Ala Ala Glu Ala Leu Asn Ala Ser
20 25 30

Ser Lys Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 10
<211> LENGTH: 70
<212> TYPE: PRT
<213> ORGANISM: Tomato golden mosaic virus
<220> FEATURE:
<221> NAME/KEY: MISC_FEATURE
<222> LOCATION: (24)..(26)
<223> OTHER INFORMATION: AAA136 (Leu) mutation

<400> SEQUENCE: 10

Thr Leu Val Trp Gly Glu Phe Gln Val Asp Gly Arg Ser Ala Arg Gly
1 5 10 15

Gly Cys Gln Thr Ser Asn Asp Leu Leu Leu Glu Ala Leu Asn Ala Ser
20 25 30

Ser Lys Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 11
<211> LENGTH: 356
<212> TYPE: PRT

-continued

```
<213> ORGANISM: Tomato golden mosaic virus
<220> FEATURE:
<221> NAME/KEY: misc_feature
<222> LOCATION: (354)..(354)
<223> OTHER INFORMATION: Xaa can be any naturally occurring amino acid

<400> SEQUENCE: 11

Met Pro Ser His Pro Arg Phe Gln Ile Asn Ala Lys Asn Tyr Phe Leu
1               5                   10                  15

Thr Tyr Pro Gln Cys Ser Leu Ser Lys Glu Glu Ser Leu Ser Gln Leu
            20                  25                  30

Gln Ala Leu Asn Thr Pro Ile Asn Lys Lys Phe Ile Lys Ile Cys Arg
        35                  40                  45

Glu Leu His Glu Asp Gly Gln Pro His Leu His Val Leu Ile Gln Phe
    50                  55                  60

Glu Gly Lys Tyr Cys Cys Gln Asn Gln Arg Phe Phe Asp Leu Val Ser
65                  70                  75                  80

Pro Thr Arg Ser Ala His Phe His Pro Asn Ile Gln Arg Ala Lys Ser
                85                  90                  95

Ser Ser Asp Val Lys Thr Tyr Ile Asp Lys Asp Gly Asp Thr Leu Val
            100                 105                 110

Trp Gly Glu Phe Gln Val Asp Gly Arg Ser Ala Arg Gly Gly Cys Gln
        115                 120                 125

Thr Ser Asn Asp Ala Ala Ala Glu Ala Leu Asn Ala Ser Ser Lys Glu
    130                 135                 140

Glu Ala Leu Gln Ile Ile Arg Glu Lys Ile Pro Glu Lys Tyr Leu Phe
145                 150                 155                 160

Gln Phe His Asn Leu Asn Ser Asn Leu Asp Arg Ile Phe Asp Lys Thr
                165                 170                 175

Pro Glu Pro Trp Leu Pro Pro Phe His Val Ser Ser Phe Thr Asn Val
            180                 185                 190

Pro Asp Glu Met Arg Gln Trp Ala Glu Asn Tyr Phe Gly Lys Ser Ser
        195                 200                 205

Ala Ala Arg Pro Glu Arg Pro Ile Ser Ile Ile Ile Glu Gly Asp Ser
    210                 215                 220

Arg Thr Gly Lys Thr Met Trp Ala Arg Ser Leu Gly Pro His Asn Tyr
225                 230                 235                 240

Leu Ser Gly His Leu Asp Leu Asn Ser Arg Val Tyr Ser Asn Lys Val
                245                 250                 255

Glu Tyr Asn Val Ile Asp Asp Val Thr Pro Gln Tyr Leu Lys Leu Lys
            260                 265                 270

His Trp Lys Glu Leu Ile Gly Ala Gln Arg Asp Trp Gln Thr Asn Cys
        275                 280                 285

Lys Tyr Gly Lys Pro Val Gln Ile Lys Gly Gly Ile Pro Ser Ile Val
    290                 295                 300

Leu Cys Asn Pro Gly Glu Gly Ala Ser Tyr Lys Val Phe Leu Asp Lys
305                 310                 315                 320

Glu Glu Asn Thr Pro Leu Lys Asn Trp Thr Phe His Asn Ala Lys Phe
                325                 330                 335

Val Phe Leu Asn Ser Pro Leu Tyr Gln Ser Ser Thr Gln Ser Ser Asn
            340                 345                 350

Asn Xaa Asn Ser
        355

<210> SEQ ID NO 12
```

-continued

<211> LENGTH: 70
<212> TYPE: PRT
<213> ORGANISM: Tomato golden mosaic virus

<400> SEQUENCE: 12

```
Thr Leu Val Trp Gly Glu Phe Gln Val Asp Gly Arg Ser Ala Arg Gly
1               5                   10                  15

Gly Cys Ala Ala Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70
```

<210> SEQ ID NO 13
<211> LENGTH: 70
<212> TYPE: PRT
<213> ORGANISM: Tomato golden mosaic virus

<400> SEQUENCE: 13

```
Thr Leu Val Trp Gly Glu Phe Gln Val Asp Gly Arg Ser Ala Arg Gly
1               5                   10                  15

Gly Cys Gln Thr Ser Ala Ala Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70
```

<210> SEQ ID NO 14
<211> LENGTH: 70
<212> TYPE: PRT
<213> ORGANISM: Tomato golden mosaic virus

<400> SEQUENCE: 14

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Ala Ala Leu Ala Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70
```

<210> SEQ ID NO 15
<211> LENGTH: 70
<212> TYPE: PRT
<213> ORGANISM: Tomato golden mosaic virus

<400> SEQUENCE: 15

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
```

```
                20                  25                  30
Ser Ala Ala Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70

<210> SEQ ID NO 16
<211> LENGTH: 70
<212> TYPE: PRT
<213> ORGANISM: Tomato golden mosaic virus

<400> SEQUENCE: 16

Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
                20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Ala Thr Pro Ala Pro
65                  70

<210> SEQ ID NO 17
<211> LENGTH: 31
<212> TYPE: DNA
<213> ORGANISM: Artificial sequence
<220> FEATURE:
<223> OTHER INFORMATION: Mutagenesis oligonucleotide for FQ118 (Ala13)

<400> SEQUENCE: 17
cacttcgacc gtcgaccgcg gcttctcccc a                              31

<210> SEQ ID NO 18
<211> LENGTH: 31
<212> TYPE: DNA
<213> ORGANISM: Artificial sequence
<220> FEATURE:
<223> OTHER INFORMATION: Mutagenesis oligonucleotide for D120 (Ala14)

<400> SEQUENCE: 18
cacttcggcc ggcgaccgcg gcttctcccc a                              31

<210> SEQ ID NO 19
<211> LENGTH: 35
<212> TYPE: DNA
<213> ORGANISM: Artificial sequence
<220> FEATURE:
<223> OTHER INFORMATION: Mutagenesis oligonucleotide for RS-R125 (Ala1)

<400> SEQUENCE: 19
gcaacctcct gcagcggccg caccgtcgac ctgga                          35

<210> SEQ ID NO 20
<211> LENGTH: 35
<212> TYPE: DNA
<213> ORGANISM: Artificial sequence
<220> FEATURE:
<223> OTHER INFORMATION: Mutagenesis oligonucleotide for QT130 (Ala2)

<400> SEQUENCE: 20
```
cagcgtcgtt gctagctgcg caacctcctc tagca                           35

<210> SEQ ID NO 21
<211> LENGTH: 29
<212> TYPE: DNA
<213> ORGANISM: Artificial sequence
<220> FEATURE:
<223> OTHER INFORMATION: Mutagenesis oligonucleotide for ND133 (Ala3)

<400> SEQUENCE: 21
ctgctgcagc ggccgcagat gtttggcaa                                 29

<210> SEQ ID NO 22
<211> LENGTH: 35
<212> TYPE: DNA
<213> ORGANISM: Artificial sequence
<220> FEATURE:
<223> OTHER INFORMATION: Mutagenesis oligonucleotide for E--N140 (Ala4)

<400> SEQUENCE: 22
ggaagaagca gctaacgcgg ccgctgcagc gtcgt                           35

<210> SEQ ID NO 23
<211> LENGTH: 35
<212> TYPE: DNA
<213> ORGANISM: Artificial sequence
<220> FEATURE:
<223> OTHER INFORMATION: Mutagenesis oligonucleotide for KEE146 (Ala5)

<400> SEQUENCE: 23
cagcgtcgtt agcagctgcg caacctcctc tagca                           35

<210> SEQ ID NO 24
<211> LENGTH: 32
<212> TYPE: DNA
<213> ORGANISM: Artificial sequence
<220> FEATURE:
<223> OTHER INFORMATION: Mutagenesis oligonucleotide for REK154 (Ala6)

<400> SEQUENCE: 24
ttctgggatt gcggccgcaa ttatctgcag gg                              32

<210> SEQ ID NO 25
<211> LENGTH: 35
<212> TYPE: DNA
<213> ORGANISM: Artificial sequence
<220> FEATURE:
<223> OTHER INFORMATION: Mutagenesis oligonucleotide for EKY159 (Ala7)

<400> SEQUENCE: 25
gaactgaaat aaagcggccg ctgggatttt ctctc                           35

<210> SEQ ID NO 26
<211> LENGTH: 42
<212> TYPE: DNA
<213> ORGANISM: Artificial sequence
<220> FEATURE:
<223> OTHER INFORMATION: Mutagenesis oligonucleotide for Q-HN165 (Ala8)

<400> SEQUENCE: 26
gctatttaga gcggcgaacg caaataaata tttttctggg at                   42

<210> SEQ ID NO 27
<211> LENGTH: 36
<212> TYPE: DNA

-continued

```
<213> ORGANISM: Artificial sequence
<220> FEATURE:
<223> OTHER INFORMATION: Mutagenesis oligonucleotide for N-DR172 (Ala9)

<400> SEQUENCE: 27
atcaaatatc gcagctagcg cgctatttag attgtg                         36

<210> SEQ ID NO 28
<211> LENGTH: 33
<212> TYPE: DNA
<213> ORGANISM: Artificial sequence
<220> FEATURE:
<223> OTHER INFORMATION: Mutagenesis oligonucleotide for K--E179 (Ala10)

<400> SEQUENCE: 28
gaagccatgg cgccggagtc gcatcaaata tcc                            33

<210> SEQ ID NO 29
<211> LENGTH: 37
<212> TYPE: DNA
<213> ORGANISM: Artificial sequence
<220> FEATURE:
<223> OTHER INFORMATION: Mutagenesis oligonucleotide for AAA136 (Leu)

<400> SEQUENCE: 29
gaagcattta aggcctctag tagaaggtcg ttagatg                        37

<210> SEQ ID NO 30
<211> LENGTH: 54
<212> TYPE: DNA
<213> ORGANISM: Artificial sequence
<220> FEATURE:
<223> OTHER INFORMATION: Mutagenesis oligonucleotide for E--N140 +
      KEE146 (Ala4+5)

<400> SEQUENCE: 30
tctgcagggc tgcggccgcg gaagaagcag ctaacgcggc cgctgcagcg tcgt      54
```

GEMINIVIRUS RESISTANT TRANSGENIC PLANTS

This application claims the benefit of provisional No. 60/125,004 filed Mar. 18, 1999.

FIELD OF THE INVENTION

The present invention relates to transgenic plants with increased resistance to geminivirus infection, and the mutants of the AL1/C1 (Rep) geminivirus protein useful for producing such plants. Methods of screening for suitable mutants are also provided.

BACKGROUND OF THE INVENTION

The geminiviruses are a large and diverse family of plant DNA viruses, with circular single-stranded (ss) DNA genomes that replicate through circular double stranded DNA intermediates. See Hanley-Bowdoin et al., *Cri. Rev. Plant Sci.* 18:71 (1999); Lazarowitz, *Crit. Rev. Plant Sci.* 11:327 (1992); Timmermans et al., *Annu. Rev. Plant Physiol.* 45:79 (1994). Viral DNA replication, which results in both single and double stranded viral DNAs in large amounts, involves the expression of only a small number of viral proteins that are involved in either replication or viral transcription. The geminiviruses appear to rely primarily on the machinery of the host to copy their genomes and express their genes, including the nuclear DNA and RNA polymerases of their plant hosts. These properties of geminiviruses are unusual among plant viruses, most of which are RNA viruses or replicate through RNA intermediates using virus-encoded replicases. Geminiviruses infect a broad variety of plants and cause significant crop losses worldwide.

Geminiviruses are subdivided on the basis of host range in either monocots or dicots, genome structure, and insect vector. Subgroup I geminiviruses (also known as Mastreviruses) are transmitted by leafhoppers and infect primarily monocots, although Subgroup I geminiviruses that infect dicots are known. Subgroup II geminiviruses (also known as Curtoviruses) are transmitted by leafhoppers and infect dicots. Subgroup III geminiviruses (also known as Begomoviruses) are transmitted by whiteflys and infect dicots. Subgroups I & II viruses have genomes comprising a single ssDNA component; Subgroup III geminiviruses typically have a bipartite genome comprising two similarly sized DNAs (usually termed A and B), as illustrated by African cassava mosaic virus (ACMV), tomato golden mosaic virus (TGMV) and potato yellow mosaic virus. However, monopartite geminiviruses that infect dicots are known, for example Tomato Yellow Leaf Curl Virus (TYLCV). The genomes of monopartite Subgroup II and III geminiviruses have an arrangement of genes similar to the AL1, AL2 and AL3 genes found on the A DNA component of bipartite Subgroup III geminiviruses.

Subgroup II viruses are also divided into "old world" and "new world" viruses, a division based on evolutionary divergence.

For successful infection of plants by bipartite geminiviruses, both the A and B genomic components are required. Sequence analysis of the two genome components reveals six open reading frames (ORFs); four of the ORFs are encoded by DNA A and two by DNA B. On both components, the ORFs diverge from a conserved 230 nucleotide intergenic region (common region) and are transcribed bidirectionally from double stranded replicative form DNA. The ORFs are named according to genome component and orientation relative to the common region (i.e., left versus right (L/R), or virion versus complementary sense (V/C)). Certain proteins are known to be involved in the replication of viral DNA (REP genes). See, e.g., Elmer et al., *Nucleic Acids Res.* 16:7043 (1988); Hatta and Francki, *Virology* 92:428 (1979).

The A genome component contains all viral information necessary for the replication and encapsidation of viral DNA, while the B component encodes functions required for movement of the virus through the infected plant. The DNA A component of these viruses is capable of autonomous replication in plant cells in the absence of DNA B when inserted as a greater than full length copy into the genome of plant cells, or when a copy is transiently introduced into plant cells. In monopartite geminivirus genomes, the single genomic component contains all viral information necessary for replication, encapsidation, and movement of the virus.

Geminiviruses cause substantial losses among economically important crops, including tomato, bean and cucurbit. Current strategies to control geminivirus infections target the insect vectors that carry the viruses. However, the use of insecticides to control or combat a geminivirus infection can be expensive and inefficient. Additionally, insect hosts may vary in their susceptibility to available insecticides, and resistance to insecticides may develop over time. See Markham et al., *Pestic. Sci.* 42:123 (1994).

Varied approaches have been used in attempts to generate geminivirus-resistant plants, including classical breeding and transgenic approaches, with limited success. Unlike plant RNA viruses, the introduction of geminivirus sequences into transgenic plants does not confer resistance and, conversely, frequently results in the production of functional viral proteins (Hayes and Buck, *Nucleic Acids Res.* 17:10213 (1989); Hanley-Bowdoin et al., *Proc. Natl. Acad. Sci. USA* 87:1446 (1990)). Kunik et al. report transgenic tomatoes that contain a geminivirus coat protein gene (Kunik et al., *BioTechnology* 12:500 (1994)). Expression of antisense RNAs against geminivirus replication proteins in transgenic plants reduces the level of viral DNA accumulation up to 70% (Day et al., *Proc. Natl. Acad. Sci. USA* 88:6721 (1991)), to a level that is still sufficient to confer wild type viral symptoms (Hanley-Bowdoin et al., *Plant Cell* 1:1057 (1989)). Similarly, the presence of defective-interfering replicons in transformed plants can reduce the level of viral DNA accumulation by about 70% (Frischmuth and Stanley, *Virology* 200:826 (1994)). The antisense RNAs and defective-interfering replicons function best against their cognate viruses (Bejarano et al., *Plant Mol. Biol.* 24:241 (1994)), further limiting their usefulness. Antisense RNA targeted to mRNA of the Rep protein (encoded by the C1 gene) was used by Bendahmane and Gronenborn to produce transgenic *Nicotiana benthamiana* plants with altered responses to TYLCV. *Plant Mol. Biol.* 33:351(1997)

Accordingly, it is desirable to devise new strategies to control geminivirus infection.

SUMMARY OF THE INVENTION

A first aspect of the present invention is a plant comprising transformed plant cells, said transformed plant cells containing a heterologous nucleic acid construct comprising, in the 5' to 3' direction, a promoter operable in said plant cells, a nucleic acid sequence encoding a mutant AL1 protein, where said nucleic acid sequence is located downstream from said promoter and operatively associated therewith, and comprising a mutation in the Rb binding region, whereby binding of said mutant AL1 protein to a plant Rb protein is reduced compared to binding which would occur in the presence of a wild-type AL1 protein; and a mutation in the AL1 protein, whereby said mutant AL1 protein suppresses viral replication compared to that which would occur in the presence of a wild-type AL1 protein; and a termination sequence positioned downstream from said nucleic acid sequence and operatively associated therewith, wherein expression of said mutant AL1 protein increases resistance of said plant to infection by at least one geminivirus, compared to a non-transformed control.

A further aspect of the present invention is a method of making a transgenic plant having increased resistance to geminivirus infection. The method comprises providing a plant cell capable of regeneration; transforming the plant cell with a DNA construct comprising, in the 5' to 3' direction, (a) a promoter operable in said plant cells, (b) a nucleic acid sequence encoding a mutant AL1 protein, said nucleic acid sequence located downstream from said promoter and operatively associated therewith, and comprising i) a mutation in the Rb binding region, whereby binding of said mutant AL1 protein to a plant Rb protein is reduced compared to binding which would occur in the presence of a wild-type AL1 protein; and ii) a mutation in the AL1 protein, whereby said mutant AL1 protein suppresses viral replication compared to that which would occur in the presence of a wild-type AL1 protein; and (c) a termination sequence positioned downstream from said nucleic acid sequence and operatively associated therewith; and then regenerating a transgenic geminivirus-resistant plant from said transformed plant cell, wherein expression of said mutant AL1 protein increases resistance of said plant to infection by at least one geminivirus, compared to a non-transformed control.

A further aspect of the present invention is a nucleic acid construct comprising an expression cassette, which construct comprises, in the 5' to 3' direction, a promoter operable in a plant cell, a nucleic acid sequence encoding a mutant AL1 protein, said nucleic acid sequence located downstream from said promoter and operatively associated therewith, and comprising a mutation in the Rb binding region, whereby binding of said mutant AL1 protein to a plant Rb protein is reduced compared to binding which would occur in the presence of a wild-type AL1 protein; and ii) a mutation in the AL1 protein, whereby said mutant AL1 protein suppresses viral replication compared to that which would occur in the presence of a wild-type AL1 protein; and a termination sequence positioned downstream from said nucleic acid sequence and operatively associated therewith.

A further aspect of the present invention is a method of producing nucleic acid constructs useful in conferring increased geminivirus-resistance to plants, comprising, screening mutants of a geminivirus AL1 protein to identify mutations that suppress the ability of the AL1 protein to bind to a plant Rb protein; preparing a nucleic acid molecule encoding an AL1 protein having said mutation, and further having a mutation that suppresses geminivirus replication compared to that which would occur in the presence of a wild-type AL1 protein; and preparing a nucleic acid construct comprising, in the 5' to 3' direction, a promoter operable in a plant cell, a nucleic acid sequence encoding said mutant AL1 protein, said nucleic acid sequence located downstream from said promoter and operatively associated therewith, and a termination sequence positioned downstream from said nucleic acid sequence and operatively associated therewith.

A further aspect of the present invention is a nucleic acid construct comprising an expression cassette, which construct comprises, in the 5' to 3' direction: a promoter operable in a plant cell, a nucleic acid sequence encoding a mutant AL1 protein, said nucleic acid sequence located downstream from said promoter and operatively associated therewith, and comprising: a mutation in the oligomerization domain, whereby binding of said mutant AL1 protein to wildtype AL1 protein is reduced compared to binding which would occur with a wild-type AL1 protein; and a mutation in the AL1 protein, whereby said mutant AL1 protein suppresses viral replication compared to that which would occur in the presence of a wild-type AL1 protein; and a termination sequence positioned downstream from said nucleic acid sequence and operatively associated therewith.

BRIEF DESCRIPTION OF THE DRAWINGS

FIG. 1 shows the amino acid sequence of TGMV Rep, from amino acid 110–179, and the sequences of alanine and leucine substitution mutants. Underlined amino acids correspond to a conserved helix-loop-helix motif found in the Rep proteins of all geminiviruses; double underlined amino acids show the substitutions.

FIG. 2A diagrams the AL1 protein showing the positions of the three conserved cleavage motifs (solid boxes), two predicted pairs of helices (hatched circles), and the ATP binding site (hatched box). The domains for DNA binding and cleavage/ligation activity are indicated above by solid lines and the oligomerization domain is shown as a dashed line. Solid lines below the AL1 diagram mark the sizes of the truncated proteins and are designated by their N- and C-terminal amino acids. The boxed region indicates the limits of the core oligomerization domain.

FIG. 2B shows the results of an immunoblot assay to detect protein interactions of C-terminal truncated proteins with full length GSTAL1. Total extracts from insect cells co-expressing GST-AL1 with truncated AL1 proteins were incubated with glutathione-sepharose, washed and eluted in SDS-sample buffer. Bound AL1 proteins were visualized by immunoblot assays. Input (lanes 1–3) and bound (lanes 4–6) fractions were resolved by SDS-polyacrylamide gel electrophoresis and analyzed by immunoblotting. AL1 1–180 (lanes 1 and 4), AL1 1–168 (lanes 2 and 5), AL1 1–158 (lanes 3 and 6).

FIG. 2C shows the results of an immunoblot assay to detect protein interactions of N-terminal truncated proteins with full length GST-AL1. Total extracts from insect cells co-expressing GST-AL1 with truncated AL1 proteins were incubated with glutathione-sepharose, washed and eluted in SDS-sample buffer. Bound AL1 proteins were visualized by immunoblot assays. Input (lanes 1–3) and bound (lanes 4–6) fractions were resolved by SDS-polyacrylamide gel electrophoresis and analyzed by immunoblotting. AL1 134–352 (lanes 1 and 4), AL1 147–352 (lanes 2 and 5) and AL1 159–352 (lanes 3 and 6).

FIG. 2D show the results of co-purification assays performed with GST-AL1 119–180 and N-terminal truncated AL1 119–352 (lanes 1 and 5), AL1 134–352 (lanes 2 and 6), AL1 147–352 (lanes 3 and 7), and AL1 158–352 (lanes 4 and 8).

Figure 3:
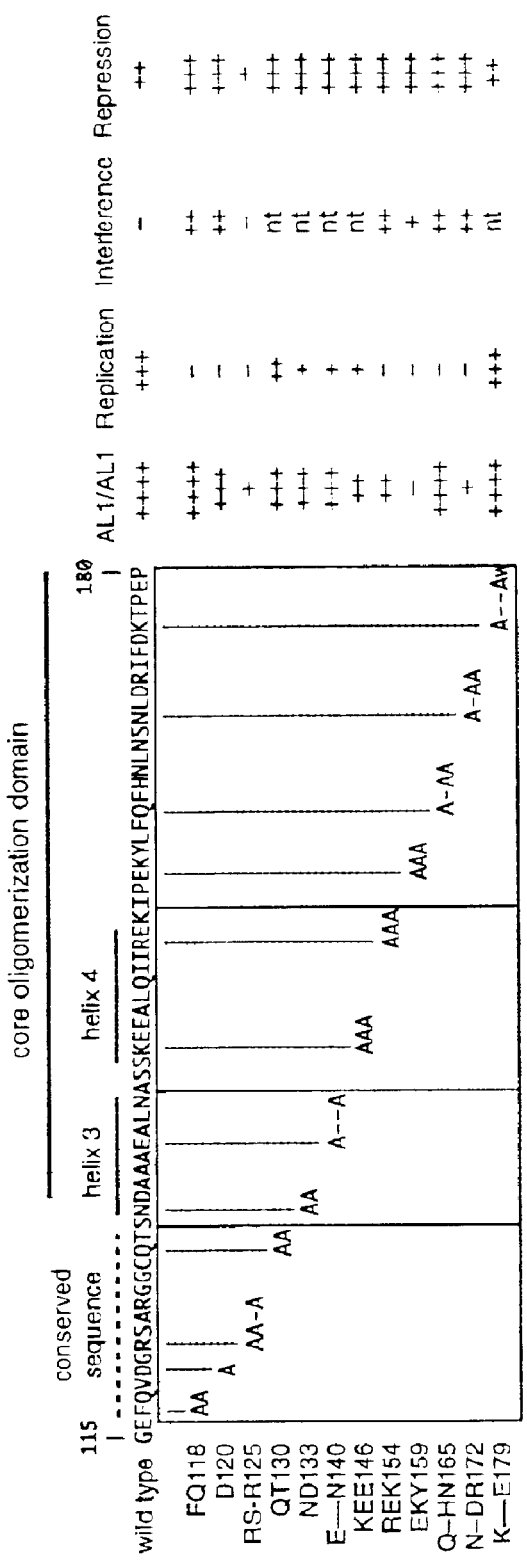
FIG. 3 shows mutations generated in the oligomerization domain of AL1, and their characteristics.

(lane 1), AL1 E—N140 (Ala4, lane 3), AL1 KEE146 (Ala5, lane 4), AL1 REK154 (Ala6, lane 5), AL1 EKY159 (Ala7, lane 6), AL1 Q-HN165 (Ala8, lane 7), AL1 N-DR172 (Ala9, lane 8), and AL1 K-E179 (Ala10, lane 9). Wild type AL1 was also co-expressed with GST alone (lane 2).

Figure 4A:
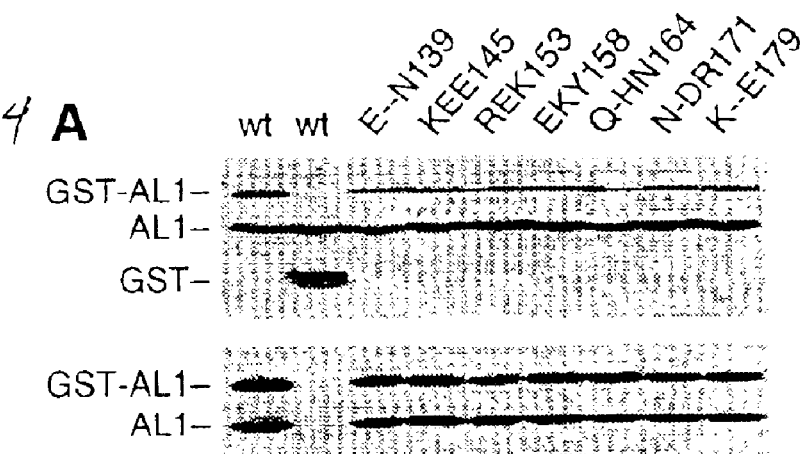
FIG. 4A shows oligomerization properties of AL1 proteins with mutations in the core oligomerization domain in insect cells. Protein interactions were assayed as described in FIG. 1. Mutant AL1 proteins co-expressed with full length GST-AL1 were extracted (top) and bound to glutathione-sepharose (bottom). Lanes correspond to wild type AL1
Figure 4B:
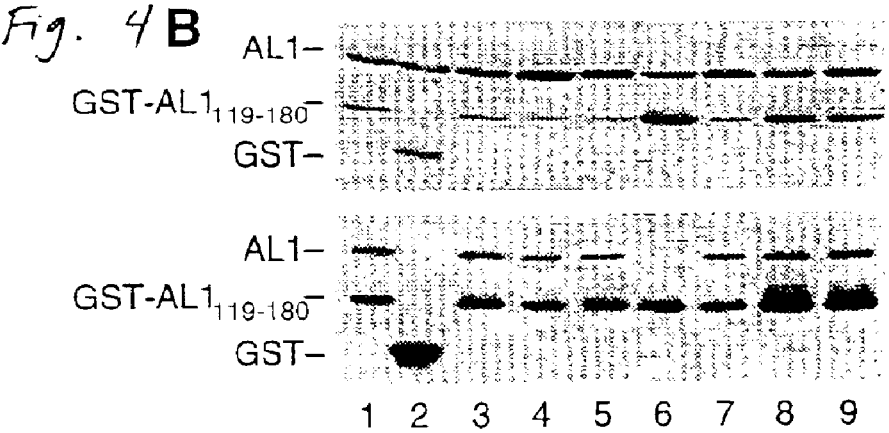

FIG. 4B shows oligomerization properties of AL1 proteins with mutations in the core oligomerization domain in insect cells. Protein interactions were assayed as described in FIG. 1. Mutant AL1 proteins were co-expressed with GST-AL1 119–180. The lanes are as described in panel A.

Figure 4C:
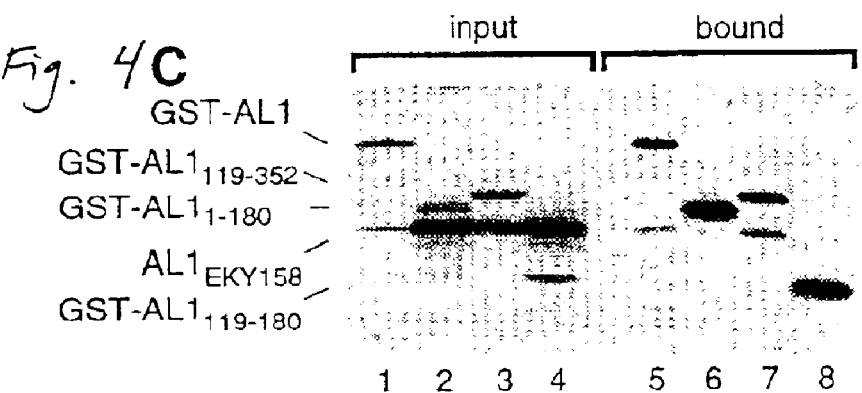

FIG. 4C The mutant AL1 EKY159 was co-expressed with GST-AL1 fusion proteins of full-length and truncated AL1. Lanes 1–4 show AL1 proteins bound to glutathione-sepharose. The GST-AL1 proteins assayed were full-length GST-AL1 (lanes 1 and 5), GST-AL1(1–180) (lanes 2 and 6), GST-AL1(119–352)(lanes 3 and 7), and GST-AL1 (119–180) (lanes 4 and 8).

Figure 5A:
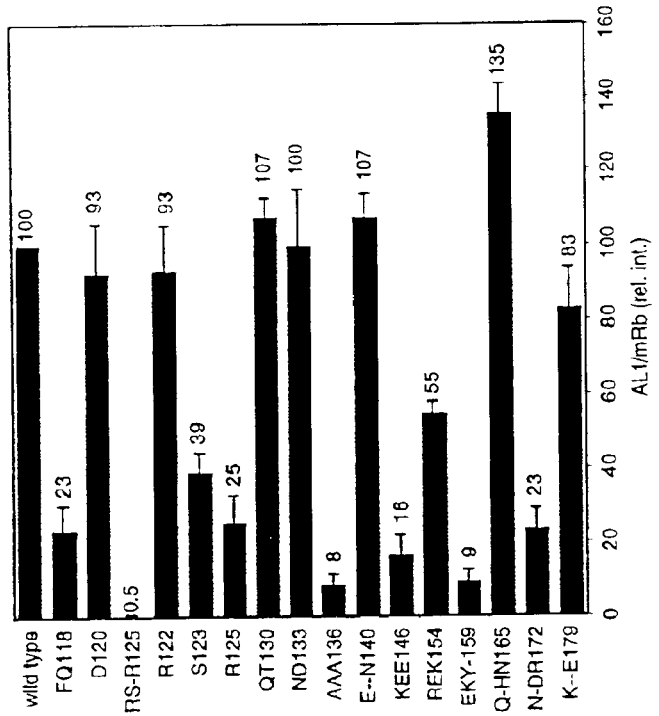

FIG. 5A shows the interaction of mutant AL1 proteins with wild type AL1 in a yeast dihybrid assay. Expression cassettes for wild type AL1 fused to the GAL4 DNA binding domain and mutant AL1 fused to the GAL4 activation domain were co-transformed into yeast. Interactions between the wild type and mutant AL1 proteins were assayed by measuring B-galactosidase.

Figure 5B:
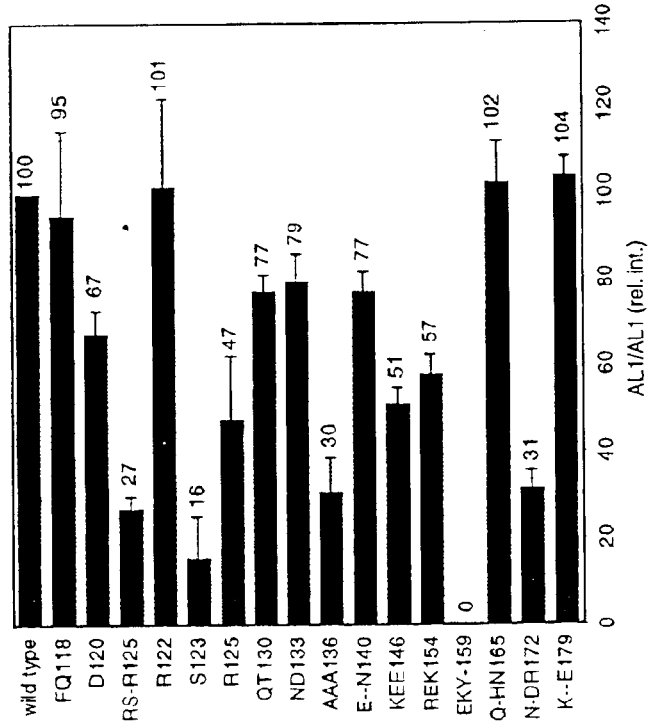

FIG. 5B shows the interaction of mutant AL1 proteins with maize Rb in a yeast dihybrid assay. Expression cassettes for maize Rb (amino acids 214–866, Ach et al., *Mol. Cell. Biol.* 17:5077 (1997)) fused to the GAL4 binding domain and mutant AL1 fused to the GAL4 DNA activation domain were co-transformed into yeast. Interactions between the wild type and mutant AL1 proteins were assayed by measuring B-galactosidase.

Figure 6A:
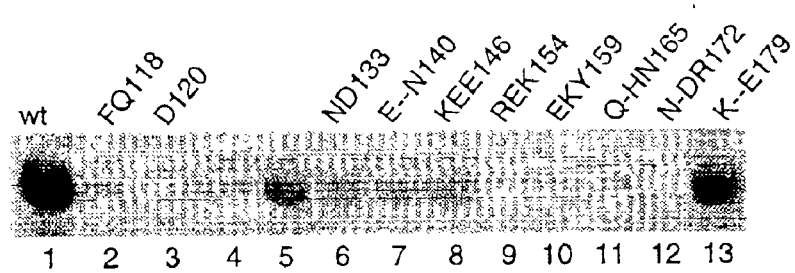

FIG. 6A is a gel showing that transient replication of TGMV B DNA is impaired by mutations in the AL1 oligomerization domain and upstream stabilizing region. Double-stranded DNA replication was analyzed in protoplasts co-transfected with expression cassettes for AL3, wild type or mutant AL1 proteins, and a TGMV B replicon. Total DNA was isolated three days post-transfection and analyzed by DNA gel blot hybridization using a radiolabeled TGMV B probe. Lanes correspond to transfections with wild type AL1 (lane 1), AL1 FQ118 (Ala13, lane 2), AL1 D120 (Ala14, lane 3), AL1 RS-R125 (Ala 1, lane 4), AL1 QT130 (Ala2, lane 5), AL1 ND133 (Ala3, lane 6), AL1 E—N140 (Ala4, lane 7), AL1 KEE146 (Ala5, lane 8), AL1 REK154 (Ala6, lane 9), AL1 EKY159 (Ala7, lane 10), AL1 Q-HN165 (Ala8, lane 11), AL1 N-DR172 (Ala9, lane 12), and AL1 K—E179 (Ala10, lane 13).

Figure 6B:
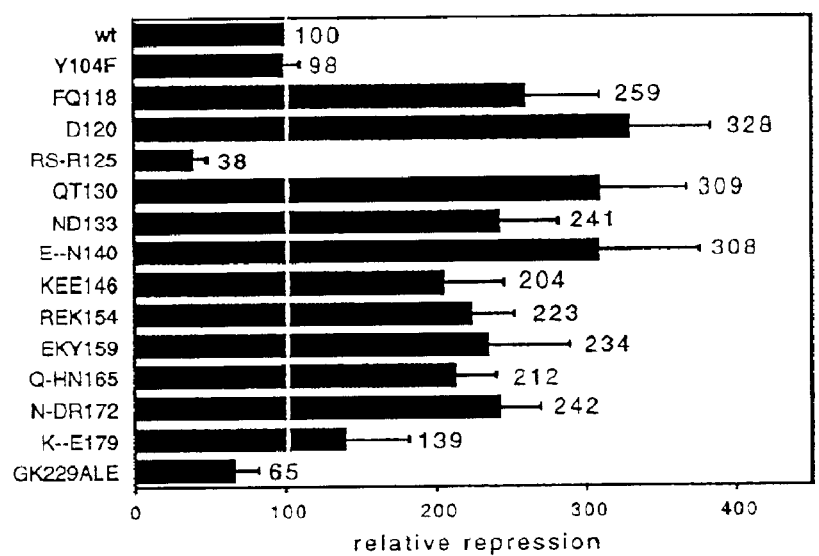

FIG. 6B graphs the relative repression of the AL1 promoter in protoplasts transfected with an expression cassettes for wild type AL1 or a mutant AL1, and a reporter with the AL1 promoter and luciferase reporter gene (luc).

Figure 7A:
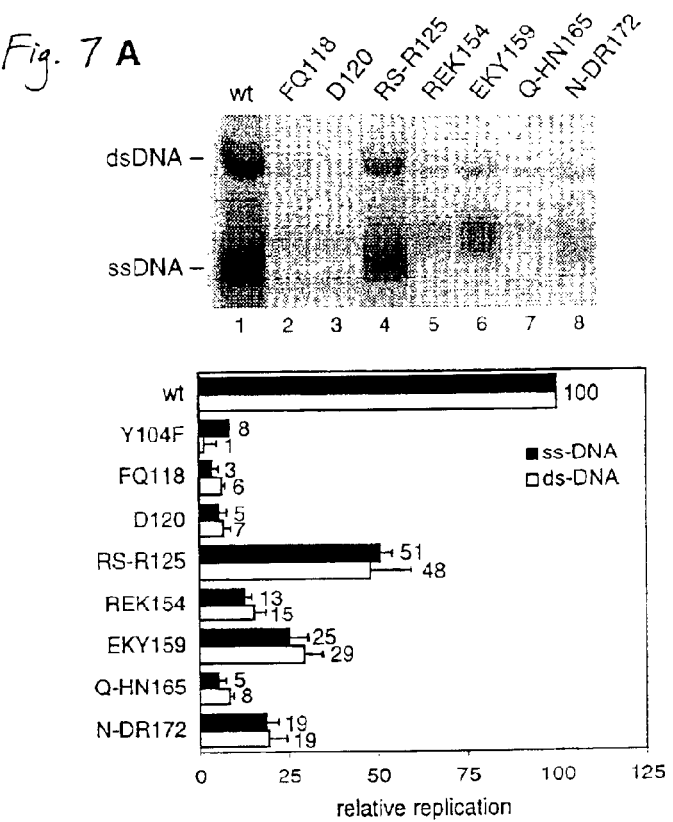

FIG. 7A shows that AL1 proteins defective for viral DNA replication interfere with TGMV A DNA replication. Protoplasts were co-transfected with 2 μg of a TGMV A replicon and 40 μg of expression cassettes coding for mutant AL1 proteins. Total DNA was isolated 3 days post-transfection and analyzed by DNA gel blot hybridization using a radiolabelled TGMV A probe. The top panel shows a representative blot of the replication interference assay. Lanes correspond to transfections of TGMV A DNA with an empty expression cassette (lane 1) and expression cassettes for AL1 FQ118 (Ala13, lane 2), AL1 D120 (Ala14, lane 3), AL1 RS-R125 (Ala1, lane 4), AL1 REK154 (Ala6, lane 5), AL1 EKY159 (Ala7, lane 6), AL1 Q-HIN165 (Ala8, lane 7), AL1 N-DR172 (Ala9, lane 8). The lower panel graphs the level of replicated viral DNA in the presence of excess mutant AL1 relative to wild type replication, averaged from at least three experiments.

Figure 7B:
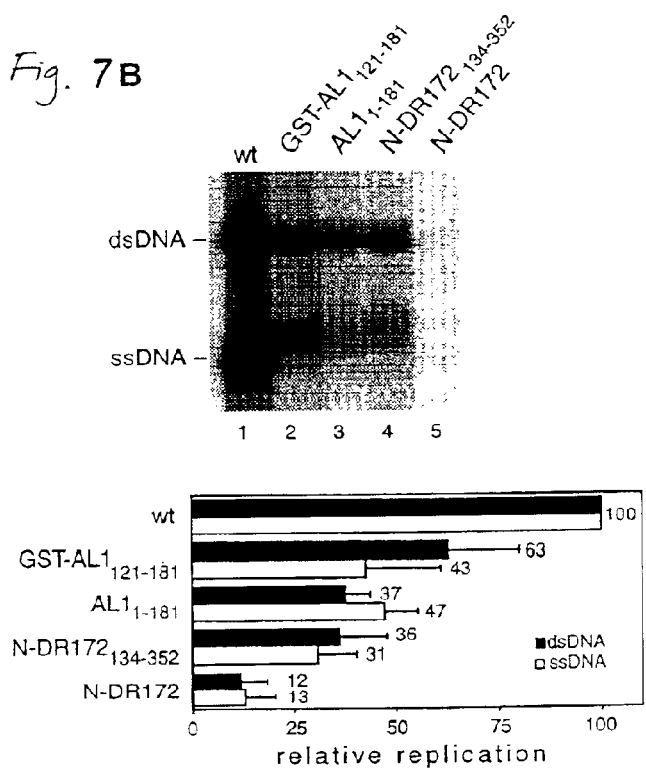

FIG. 7B shows results of experiments as described for FIG. 7A, where the top panel is a representative blot of wild type replication interference by truncated AL1 proteins. Lanes correspond to transfections of TGMV A DNA with an empty expression cassette (lane 1), GST-AL1(119–180) (lane 2), AL1(1–180) (lane 3), AL1 N-DR172(134–352) (lane 4) and AL1 N-DR172 (lane 5). The bottom panel shows the levels of replicated viral DNA in the presence of excess mutant AL1 relative to wild type replication, averaged from at least three experiments.

DETAILED DESCRIPTION

The present invention now will be described more fully hereinafter with reference to the accompanying drawings, in which preferred embodiments of the invention are shown.

The present method utilizes the expression of transdominant mutants of the geminivirus replication protein Rep, or AL1/C1, to confer increased resistance to geminiviruses in transgenic plants. While not wishing to be held to a single underlying theory, the present inventors hypothesize that the mutant proteins interfere with the replication activity of the wild type viral protein that is produced by the infecting geminiviruses, thus reducing the replication of infecting viruses and leading to enhanced resistance.

The present inventors determined that certain mutations in the AL1 sequence enhance the properties of the Rep protein that are useful in creating transgenic geminivirus resistant plants. The present invention provides nucleic acid constructs useful in producing transgenic plants with increased resistance to geminivirus infection. Prior to the present invention, transdominant mutants of the Rep (AL1) protein contained mutations in catalytic motifs, e.g., the active site for DNA cleavage (motif III) and the ATPase domain (e.g., in the P-loop sequence).

Nucleic acids according to the present invention encode a mutant AL1 protein, wherein the protein acts as a trans-dominant negative mutant, and further comprises a mutation in the Rb binding domain that decreases binding of the AL1 protein to the plant retinoblastoma protein, compared to that which would occur in the presence of wild type AL1. In TGMV virus, the Rb binding domain is found between amino acids 100–180. The present mutation Ala5 (EKY159) and Leu are examples of such mutations, resulting in decreased Rb binding compared to wildtype AL1.

Nucleic acids according to the present invention encode a mutant AL1 protein, wherein the protein acts as a trans-dominant negative mutant, and has a mutation in the oligomerization domain that decreases binding of the mutant AL1 to wildtype AL1, compared to that which would occur in the presence of only wildtype AL1. Such mutants result in decreased replication of infecting geminiviruses. The present mutation Ala5 (EKY159) and Leu are examples of such mutations, resulting in decreased AL1/AL1 binding compared to wildtype AL1.

Nucleic acids according to the present invention encode a mutant AL1 protein, wherein the protein acts as a trans-dominant negative mutant, and further comprises a mutation that results in enhanced repression of the viral promoter.

Specific examples of AL1 mutations in the TGMV viral genome are provided herein. It will be apparent to those skilled in the art that, in related geminiviruses, the retinoblastoma binding domain and oligomerization domain can be determined as shown herein. Mutations similar to the present TGMV mutations for other geminiviruses can thus be obtained.

Geminiviruses

The Geminiviridae family consists of three subgroups that differ with respect to insect vector, host range and genome structure. Subgroup I includes leafhopper-transmitted viruses that generally infect monocot plants and have single-component genomes. Subgroup III includes whitefly-transmitted viruses that infect dicot plants and most commonly have bipartite genomes. Subgroup II viruses are transmitted by leafhoppers and have single-component genomes like Subgroup I, but infect dicot plants like Subgroup III. Members of the three subgroups use similar replication and transcription strategies, although differences exist.

Geminiviruses have small genomes consisting of either one or two circular ss DNA molecules ranging from about 2.5 to about $3 \times 10^3$ nucleotides in size. The genomic DNAs contain divergent coding sequences separated by 5' intergenic regions. The coding capacity of the genomes varies among the different subgroups. Subgroup I viruses specify four open reading frames for polypeptides greater than 10 kDa, whereas subgroup II and III viruses encode six to seven open reading frames. There are currently two nomenclatures for geminivirus genes. The first nomenclature identifies viral genes as to whether they are specified by the virion (V) or complementary (C) sense DNA strands, whereas the second designates genes with respect to the left (L) or right (R) of the 5' intergenic region. The C and L designations are equivalent, as are the V and R designations.

The genomes of Subgroup III geminiviruses typically consist of two DNA components, designated A and B. Both components are required for efficient infection of host plants. The A component encodes all of the information necessary for viral replication and encapsidation, whereas the B component cannot replicate in the absence of A DNA, but is required for systemic movement of the virus and symptom production in infected plants. The A component typically contains five open reading frames (ORFs), four of which (AL1/C1, AL2/C2, AL3/C3 and AL4/C4) are specified by overlapping sequences on the complementary strand. Mutations in the AL3 gene result in severely delayed and attenuated symptoms (Morris et al., *J. Gen. Virol.* 72:1205 (1991); Etessami et al., *J. Gen. Virol.* 72:1005 (1991); Sung and Coutts, *J. Gen. Virol.* 76:1773 (1995)).

AL1/C1 (Rep) and AL3/C3 (Ren) proteins are involved in geminivirus replication, and AL1/C1 (Rep) and AL2/C2 proteins act in regulating viral gene expression. Mutation of the AL1 open reading frame was shown to block viral replication, whereas an AL3 mutant resulted in reduced DNA levels (Sunter et al., *Virology* 179:69 (1990); Sung and Coutts, *J. Gen. Virol.* 76:1773 (1995)). Additionally, transgenic plants that contained the AL1 gene and constitutively expressed the Rep protein in the absence of AL3 supported replication of DNA B, demonstrating that Rep is sufficient for replication in the presence of host factors. (Hanley-Bowdoin et al., *Proc. Natl. Acad. Sci. USA* 87:1446 (1990); Elmer et al. *Nucleic Acids Res.* 16:7043 (1988)).

The genomes of all geminiviruses employ the same general strategy for duplication and expression: a rolling circle replication system that amplifies ssDNA and produces dsDNAs that serve as templates for replication and transcription. The double-stranded form of DNA is divergently transcribed from a 5' intergenic region that also includes the plus-strand origin of replication.

Rolling circle replication is a two-step process; synthesis of the leading and lagging-strand DNA are separate events. The single-stranded 'plus' strand is first used as a template for the synthesis of the 'minus' strand, resulting in a double-stranded replicative form (RF). The replicative form then serves as a template for plus-strand synthesis to generate free ssDNA. A site-specific nick primes plus-strand DNA synthesis (a hallmark of rolling circle replication systems). In subgroup I viruses, minus-strand synthesis appears to be primed by RNA that is most likely generated by pol α/primase complex. The mechanism of minus-strand replication in subgroup III is unknown. (The plus strand corresponds to the virion strand found in both ssDNA and dsDNA; the minus strand is the complementary strand found only in dsDNA).

Thus, geminivirus replication requires two origins, one for plus-strand synthesis and one for minus-strand synthesis. The plus-strand origin of geminiviruses from all three Subgroups has been mapped to the 5' intergenic region, which also contains the promoters for virion and complementary-sense transcription. The cis elements that mediate viral replication and transcription are best characterized for the Subgroup III geminivirus, TGMV.

Geminiviruses fall into three subgroups based on their insect vector, host range and genome structure. Most dicot-infecting viruses have two genome components, designated A and B, and are transmitted by whiteflies. The single genome components of monopartite, dicot-infecting geminiviruses most resemble the A components of the bipartite viruses. The genome components are arranged similarly with 5' intergenic regions separating divergent transcription units. The 5' intergenic regions contain the viral replication origin (Revington et al., *Plant Cell* 1:985 (1989); Lazarowitz et al., *Plant Cell* 4:799 (1992)) and transcription signals (Eagle et al. *Plant Cell* 6:1157 (1994); Orozco et al., *Virology* 242:346 (1998)).

Dicot-infecting bipartite geminiviruses encode two replication proteins, AL1 and AL3, and recruit the remainder of their replication machinery from the host plant. For monopartite dicot-infecting geminiviruses such as tomato yellow leaf curl virus (TYLCV), the equivalent proteins are designated as C1 and C3, respectively. The AL1 (Rep) protein is the only viral protein essential for viral replication (Elmer et al., *Plant Mol. biol.* 10:225 (1988); Hayes and Buck, *Nucleic Acids Res.* 17:10213 (1989); Hanley-Bowdoin et al., *Proc. Natl. Acad. Sci. USA* 87:1446 (1990)). Nagar et al. report that AL1 induces the synthesis of host replication machinery in infected plant cells (Nagar et al., *Plant Cell* 7:705 (1995)). The AL3 protein is not required for replication, but enhances the level of viral DNA accumulation (Etessami et al., *J. Gen. Virol.* 72:1005 (1991); Morris et al., *J. Gen. Virol.* 72:1205 (1991)).

Methods

AL1 interferes with normal cell cycle regulation in plants and, subsequently, transgenes are silenced after several generations. Thus, AL1 proteins defective in multiple activities offer the best strategy for production of long term resistance.

The present invention is directed to the production of transgenic plants having increased resistance to geminivirus infection, to nucleic acid constructs useful in producing such plants, and to plant cells transformed with such constructs. The nucleic acid constructs contain a nucleotide encoding a mutant AL1 protein or portion of a mutant AL1 protein.

Mutant AL1 proteins according to the present invention may comprise a mutation in the Rb binding domain, such that binding of AL1 to Rb in the plant cell is decreased. Rb is a negative regulator of the cell cycle and a common target of DNA viruses. Interference with the endogenous Rb protein leads to an uncontrolled cell cycle.

Mutant AL1 proteins according to the present invention may comprise a mutation in the oligomerization domain, to produce trans-dominant negative mutants. Transdominant negative mutant proteins negatively interfere in trans with geminiviral replication during infection.

Mutant AL1 proteins according to the present invention may comprise a mutation that enhances repression of the AL1 promoter. AL1 regulates viral DNA replication and transcriptional repression by binding to a conserved sequence in the overlapping plus-strand replication origin and the AL1 promoter. Mutants with enhanced repression of the AL1 promoter will interfere with replication of infecting wild-type geminiviruses.

Specific mutant Rep proteins tested by the present inventors (see Tables 1–3) include Leu (SEQ ID NO:10), Ala1 (SEQ ID NO:2), Ala4+5 (SEQ ID NO:3), Ala6 (SEQ ID NO:4), Ala7 (SEQ ID NO:5), Ala8 (SEQ ID NO:6), Ala9 (SEQ ID NO:7), Ala13 (SEQ ID NO:8) and Ala14 (SEQ ID NO:9); these mutants are modified in the oligomerization domain and interfere with viral replication. They also display the property of enhanced repression of transcription from the Rep promoter. Because of their enhanced repression activity, the oligomerization mutants are likely to confer enhanced geminivirus resistance to transgenic plants. Mutants Ala13 (SEQ ID NO:8), Ala4+5 (SEQ ID NO:3), Ala6 (SEQ ID NO:4), and Ala7 (SEQ ID NO:5) also display impaired Rb binding and thus may be stably expressed in plants.

Accordingly, mutant AL1 proteins of the present invention may comprise any combination of (1) a mutation in the oligomerization domain (trans-dominant negative mutant), (2) a mutation in the Rb binding domain (decrease binding of AL1 to Rb) and/or (3) a mutation that increases repression of the AL1 promoter.

Transdominant negative mutants that are modified in the DNA cleavage and ATPase domains of Rep have been described (Hoogstraten, *Mol. Plant Microbe Interaction* 9:594 (1996); Hanson et al., *Virology,* 211:1 (1995); Desbiez et al., *Proc. Natl. Acad. Sci. USA* 92:5640 (1995)). Mutant AL1 proteins of the present invention may further comprise a mutation in the DNA cleavage and/or ATPase domain, where such mutations produce trans dominant negative mutants.

The present methods may thus utilize expression of a (mutant) trans-dominant viral AL1/C1 protein in transgenic plants, where the mutant contains a change in the Rb binding domain that decreases binding of the Rep protein to the Retinoblastoma homologue found in the plant to be transformed (compared to binding of the Rb homologue to wild-type AL1 protein). Mutant AL1/C1 proteins may also have a mutation in the oligomerization domain, such that viral replication is suppressed (compared to that which would occur in the presence of wild type AL1 protein). The combination of a mutation in the Rb domain as described above, and a mutation in the oligomerization domain results in a stably expressed AL1 (Rep) protein capable of suppressing the replication of infecting geminivirus.

Gronenborn and colleagues reported that *N. benthamiana* plants expressing a TYLCV C1 mutant protein are less susceptible to TYLCV infection. However, AL1 induces the synthesis of host replication proteins (Nagar, *Plant Cell* 7:705 (1995)) by interacting with plant cell cycle regulatory factors (Ach et al., *Mol. Cell. Biol.* 17:5077 (1997), and expression can be unstable in transgenic plants.

Norris et al., *Virology* 224:130–138 (1996)) reported that a truncation containing the first 210 amino acids of wild type TYLCV Rep acted as a transdominant negative mutant in cell culture and could be expressed in transgenic plants, but there is no information regarding whether truncated Rep expression can be maintained through multiple generations.

Dr. Crisanto Gutierrez (U. of Madrid) is investigating the Rb binding domain of a protein related to Rep protein (RepA) from a Subgroup I virus; this mutated RepA protein does not bind Rb. The motif in RepA is distinct with respect to sequence and location relative to the motif identified by the Ala1, Ala4+5, Ala6 and Ala7 mutations. Thus, Subgroup II and III versus I viruses may use different mechanisms to bind Rb, and there is no overlap between the present result and that of Dr. Gutierrez. Xie et al. *EMBO J.,* 14:4073 (1995); Horvath et al., *Plant. Mol. Biol.* 38:699 (1998).

The development of geminivirus resistant plants is desirable. One approach that is being tested is the expression of trans-dominant negative mutants of the geminivirus protein Rep (also called AL1 or C1), which is the only viral protein required for geminivirus replication. Trans-dominant negative mutants have been described using transient replication assays. Transdominant negative mutants that are modified in the DNA cleavage and ATPase domains of Rep have been described (Hoogstraten, *Mol. Plant Microbe Interaction* 9:594 (1996); Hanson et al., *Virology,* 211:1 (1995); Desbiez et al., *Proc. Natl. Acad. Sci. USA* 92:5640 (1995)); mutations outside of these regions have apparently not been tested. This approach has been limited at the intact plant level because of problems with stable Rep expression. The present invention provides mutant Rep proteins that can be used to overcome this limitation in the development of transgenic geminivirus resistant plants.

The geminivirus AL1 protein, which localizes to the nuclei of infected plant cells, plays key roles in geminivirus DNA replication and transcription. AL1 confers virus-specific recognition of its cognate origin of replication and initiates plus-strand DNA synthesis. AL1 also functions as a transcriptional repressor by blocking host-mediated activation of its promoter. Biochemical studies of TGMV AL1 have established that it is a sequence-specific DNA binding protein, a DNA cleavage/ligation enzyme and an ATPase. AL1 also forms large oligomers and interacts with the replication enhancer protein, AL3. All of the known activities of AL1 except for ATP hydrolysis are mediated by overlapping domains in the N-terminus of the protein.

The present inventors generated a series of AL1 mutants modified in conserved sequence and structural domains of the protein (Orozco et al., *J. Biol. Chem.* 273:24448 (1998)). Analysis of the mutant proteins established the importance of these motifs for AL1 function and revealed that DNA binding and cleavage are tightly linked, involving many of the same amino acids. However, the domain requirements for these activities can be distinguished by their dependence on AL1/AL1 interactions, which are only required for DNA binding and not for DNA cleavage/ligation.

AL1 also acts as a plant cell regulator to create an environment that facilitates efficient viral replication. Analysis of transgenic plants that constitutively expressed the TGMV viral replication protein revealed that AL1 induces the expression of a host DNA synthesis protein, proliferating cell nuclear antigen (PCNA), in mature cells. This observation suggests that AL1 is analogous to the DNA tumor antigen proteins of mammalian viruses, which induce replication machinery in their hosts by altering cell cycle and transcriptional controls. The elevated levels of PCNA mRNA detected in TGMV infected tissue and the interaction between TGMV AL1 and a plant homologue of the animal tumor suppressor protein retinoblastoma, suggest that AL1 may use similar strategies to modify plant cells.

The present invention utilizes mutant Rep proteins that are impaired for interaction with the retinoblastoma (RB) homologues from maize and Arabidopsis. Rb is a negative regulator of the cell cycle and a common target of DNA tumor viruses in mammalian cells. A Rep mutant that cannot bind Rb is likely to prove less detrimental to plants and, thus, could be combined with other mutations for stable expression of transdominant negative Rep mutants in transgenic plants.

The present inventors have devised Rep mutations suitable for use in transgenic plants. All of the mutations target one or more highly conserved residues in geminivirus Subgroup II and III rep proteins.

The use of Rep mutants that are modified in the DNA cleavage or ATPase domains to produce transgenic virus resistant plants has encountered problems with a lack of stable expression of Rep in the transgenic plants. The use of Rep mutants according to the present invention, such as one combining an oligomerization mutation with a retinoblastoma binding mutation, should not encounter the same difficulty. The present mutants Ala4+5 and Ala7 display impaired Rb binding, indicating stable expression in plants. The Leu, Ala4+5, Ala6, Ala7, Ala8, Ala9, Ala13 and Ala14 mutants act as transdominant negative mutants in transient replication assays and display enhanced repression activity in transcription assays.

Specific mutant Rep proteins tested by the present inventors (see Tables 1–3) include Leu (SEQ ID NO:10), Ala1 (SEQ ID NO:2), Ala4+5 (SEQ ID NO:3), Ala6 (SEQ ID NO:4), Ala7 (SEQ ID NO:5), Ala8 (SEQ ID NO:6), Ala9 (SEQ ID NO:7), Ala13 (SEQ ID NO:8) and Ala14 (SEQ ID NO:9); these mutants are modified in the oligomerization domain and interfere with viral replication. They also display the property of enhanced repression of transcription from the Rep promoter. Because of their enhanced repression activity, the oligomerization mutants are likely to confer enhanced geminivirus resistance to transgenic plants. Mutants Ala13, Ala4+5, Ala6, and Ala7 also display impaired Rb binding and thus may be stably expressed in plants.

Together, the Ala1, Ala4+5, Ala6, Ala7 and Ala13 mutations define a novel Rb binding domain found in the Rep proteins of Subgroup II and III geminiviruses. The Rb binding motif has also not been identified before. The Ala1 and Ala13 mutations are located in a 17 amino acid sequence that is highly conserved among most dicot-infecting geminiviruses. The Ala4+5 and Ala6 mutations are in a strongly predicted helix-loop-helix structural motif found in the Rep proteins of all geminiviruses. Hence, these mutations are likely to be broadly applicable for developing resistance strategies against all subgroups of geminiviruses. The Ala1, Ala4+5, Ala6, and/or Ala7 mutations can be incorporated into a Rep trans-dominant mutant to stabilize Rep expression. The interaction of a geminivirus Rep protein with a retinoblastoma homologue from a dicot species has not been described before.

The Ala4+5, Ala6, Ala7 and Ala13 mutations may be sufficient to confer stable geminivirus resistance to plants because they also display trans-dominant negative interfering activity in replication assays and enhanced repression activity in transcription assays.

The Ala1, Ala4+5, Ala6, Ala7, Ala13 and LEU mutants are TGMV Rep mutants containing amino acid mutations in the sequence of TGMV Rep from amino acids 110–179 (TLVWGEFQVD GRSARGGCQT SNDAAAEALN ASSKEEALQIIREKIPEKYL FQF-HINLNSNL DRIFDKTPEP (SEQ ID NO:1)), where the underlined amino acids correspond to a conserved helix-loop-helix motif found in the Rep proteins of all geminiviruses.

AL1 Protein

AL1 is a large oligomeric protein that binds double-stranded DNA, catalyzes cleavage and ligation of single-stranded DNA, and interacts with other viral and host proteins. Earlier experiments mapped the TGMV AL1 oligomerization domain between amino acids 121–181 and the DNA binding domain within amino acids 1 to 181. In the studies reported below, the present inventors used truncated TGMV AL1 proteins to refine the limits of the oligomerization domain and generated site-directed mutations in conserved charged hydrophobic residues of the domain to assess their importance in AL1 function. Nearly all of the mutants attenuated or abolished AL1-directed viral DNA replication. In contrast, the replication defective mutants were enhanced for AL1-mediated transcriptional repression. Yeast two-hybrid experiments revealed several of the mutations reduced AL1 complex stability, particularly amino acids 157–159. This mutation also disrupted protein interactions in insect cells between the full-length mutant AL1 and the AL1 oligomerization domain fused to GST. In addition, replication defective AL1 mutants interfered with DNA synthesis from wild type TGMV A, indicating that these proteins may be good candidates for use in developing geminivirus resistant transgenic plants.

AL1 has several functions in replication and transcription. AL1 mediates both virus-specific recognition of its cognate origin, and transcriptional repression by binding to the direct repeat sequence. Geminivirus replication and termination is regulated by AL1 DNA cleavage and ligation within an invariant sequence in the loop of a conserved hairpin. In addition, AL1 induces accumulation of a host replication factor, PCNA, in infected cells. Recombinant AL1 specifically binds double-stranded DNA, cleaves and ligates single-stranded DNA, and hydrolyzes ATP. Geminivirus AL1 also interacts with itself, AL3 and a plant homologue of the mammalian retinoblastoma protein, PRB1.

The domains of TGMV AL1 for double stranded DNA binding, single stranded DNA cleavage and ligation, and AL1 oligomerization have previously been mapped (Orozco et al., *J. Biol. Chem.* 272:9840 (1997); Orozco et al., *J. Biol. Chem.* 273:24448 (1998)). The AL1 DNA cleavage and ligation domain is located in the first 120 amino acids and the oligomerization domain maps between amino acids 120–181. DNA binding activity requires amino acids 1–130 for protein-DNA contacts and the AL1 oligomerization domain. The Examples provided herein report truncation studies and use of site-directed mutants to show that the oligomerization domain lies between amino acids 134 and 181 and that additional sequences outside the core domain influenced protein interactions. The mutations were also tested for their impact on viral DNA replication and transcription (in protoplasts).

Yeast dihybrid assays established that Leu, Ala1, Ala4+5, Ala6, Ala7 and Ala13 Rep mutants are impaired for interaction with the Rb homologues from maize and/or Arabidopsis. Leu, Ala4+5, Ala6 and Ala7 were shown to act as trans-dominant negative inhibitors of geminivirus replication and displayed enhanced transcriptional repression activity in Nicotiana. These activities in combination with impaired Rb binding make Leu, Ala4+5, Ala6 and Ala7 excellent candidates for conferring geminivirus resistance to plants.

EXAMPLES

TGMV AL1 regulates viral DNA replication and transcriptional repression by binding to a conserved sequence in the overlapping plus-strand replication origin and AL1 promoter. Previous experiments showed that AL1/DNA interactions require both the DNA binding domain (amino acids 1–131) and oligomerization domain (amino acids 121–181)

of AL1. To further map the oligomerization domain, AL1 truncations of TGMV AL1 (SEQ ID NO:11) were generated that deleted additional sequences from the N- and C-terminus. Truncating an additional 13 amino acids from the C-terminus abolished AL1 interactions, demonstrating that the C-terminal boundary of the oligomerization domain is between amino acids 168 and 181. The N-terminal boundary of the oligomerization domain was unclear when interactions were observed with the full length GSTAL1 protein. However, AL1 oligomerized with a GST-AL1 fusion protein containing AL1 amino acids 119–180, demonstrating that this region is sufficient to form AL1 complexes. When N-terminal truncations were co-purified with GST-AL1 119–180, protein interactions were lost when amino acids 134–147 were removed. Thus, the N-terminal boundary of the minimal oligomerization domain lies between position 134 and 147, which includes two highly predicted alpha-helices. In the presence of full-length GST-AL1, deletion of the helices resulted in near background levels of interactions, indicating that weak interactions may occur in the region 147 to 180 and that the helices are important for stable complex formation.

Alanine substitutions (see FIG. 1 and Table 3) were generated at highly conserved, charged or hydrophobic residues across the oligomerization domain to assess the contributions of specific amino acids in vitro and in vivo. The mutant proteins were first analyzed in insect cells for their effect on AL1 oligomerization. Although the amino acid changes were insufficient to disrupt interactions with the full-length GST-AL1, a more stringent assay using GST-AL1 119–180 revealed that AL1 EKY159 (Ala7) was impaired for oligomerization. However, AL1 EKY159 (Ala7) interacted with an AL1 turncation lacking the N-terminus (or, including the C-terminus) that retained the core oligomerization domain, suggesting that multiple interfaces stabilized the protein complexes. These results are consistent with the observation that additional contacts outside the core oligomerization domain contributed to interactions with wild type truncated AL1.

A yeast two-hybrid assay was employed to determine the quantitative effects of the mutations on AL1 oligomerization with the wild type protein. Consistent with the results from insect cells, AL1159 (Ala7) was the most impaired for protein interactions. Mutations that significantly altered AL1 interactions in yeast were clustered between amino acids 152 and 172, within the region defined as the minimal oligomerization domain by the truncation experiments. Mutations in the helices slightly impaired AL1 interactions compared to the 152 to 172 region, consistent with the deletion analysis suggesting that this region is also required. The alanine substitutions are not predicted to disrupt helix formation although the sequence of the helices is fairly divergent among AL1 proteins. These results indicate that the sequence is an important feature of this region. Alanine substitutions adjacent to the oligomerization domain (D120 (Ala14) and RS-R125 (Ala1)) indicate that this region contributes contacts that stabilize protein interactions.

AL1 subunits defective for viral DNA replication can potentially form complexes with wild type AL1 and interfere with normal viral DNA replication. Thus, expression vectors for seven mutant proteins were co-transfected into protoplasts with a wild type TGMV replicon. All of the mutants significantly reduced single stranded and double stranded DNA synthesis. Mutations in the conserved ATP binding site and DNA cleavage motif and a C-terminal truncation of AL1 from related geminiviruses were previously shown to interfere with replication in transgenic plants. All of these mutant proteins are candidates for developing plants resistant to geminivirus infection. However, AL1 toxicity to plant cells results in silencing of transgenes over successive generations. In addition, single mutations can potentially recombine with wild type virus to produce a functional protein. The goal of the present invention is to design non-toxic mutants of AL1 that are defective in multiple functions.

Ten of the twelve mutants enhanced repression of the AL1 promoter 2- to 4-fold above wild type AL1. AL1 K—E179 is essentially wild type for replication and AL1 oligomerization. AL1RS-R125 lacks DNA binding activity which is essential for AL1-mediated repression. No specific correlation was observed between the strength of AL1 interactions in yeast and the differential effect of the mutations on replication versus transcriptional repression. For example, AL1 EKY159 (Ala7) and AL1 Q-HN165 (Ala8) altered AL1 interactions to 0% and 102% of wild type, respectively, but displayed essentially identical effects on replication and transcription. Similarly, AL1 ND133 (Ala3) repressed expression nearly 4-fold higher than wild type AL1 and greatly reduced replication, whereas protein interactions were comparable to wild type AL1. This suggests the effect of the mutations may be attributed to changes in the structure and/or the number of AL1 subunits in the complex. Thus, structural analysis of the wild type and mutant AL1 proteins will be essential to determine the cause of the phenotypic changes observed with the mutant proteins. Ten of the mutations showed increased transcriptional repression concomitant with decreased viral replication.

TABLE 1

TGMV Rep Retinoblastoma Binding Mutants and Phenotypes

| Rep Mutant (a) | Rep1 (b) | oligomer. (c) | Rep/Rb (d) | Repress (e) | Dom. Neg (f) |
| --- | --- | --- | --- | --- | --- |
| Ala1 (SEQ ID NO:2) | neg. | 27 | 20 | 30 | + |
| Ala4 + 5 (SEQ ID NO:3) | neg. | 88 | 45 | 322 | + |
| Ala6 (SEQ ID NO:4) | neg. | 57 | 69 | 223 | + |
| Ala7 (SEQ ID NO:5) | neg. | 0 | 31 | 234 | + |
| Ala13 (SEQ ID NO:8) | neg. | 95 | 23 | 259 | + |
| Leu (SEQ ID NO:10) | neg. | 30 | 8 | 206 | + |

TABLE 2

TGMV Rep Oligomerization Mutants and Phenotypes

| Rep Mutant (a) | Rep1 (b) | oligomer. (c) | Repress (e) | Dom.Neg. (f) |
| --- | --- | --- | --- | --- |
| Ala13 (SEQ ID NO: 8) | neg. | 95 | 259 | + |
| Ala14 (SEQ ID NO: 9) | neg. | 67 | 328 | + |
| Ala1 (SEQ ID NO: 2) | neg. | 27 | 38 | + |
| Ala4 + 5 (SEQ ID NO: 3) | neg. | 88 | 322 | + |
| Ala6 (SEQ ID NO: 4) | neg. | 57 | 223 | + |
| Ala7 (SEQ ID NO: 5) | neg. | 0 | 234 | + |
| Ala8 (SEQ ID NO: 6) | neg. | 102 | 212 | + |
| Ala9 (SEQ ID NO: 7) | neg. | 31 | 242 | + |

(a) Rep sequence mutations located in the TGMV AL1 region from amino acids 120–179 (see FIG. 1)
(b) Rep1 = the capacity for each mutant to support TGMV replication in tobacco protoplasts.
(c) oligomer. = the oligomerization activity of each mutant relative to wild type (100) in yeast dihybrid assays.
(d) Rep/Rb = the Rb binding activity of each mutant relative to wild type (100) in yeast dihybrid assays (maize Rb).
(e) Repress = the ability of each mutant to repress the AL1 promoter relative to wild type Rep (100) in tobacco protoplasts.
(f) Dom. Neg. = the capacity of each mutant to interfere with replication of wild type TGMV A component in tobacco protoplasts.

TABLE 3

| Name | Amino Acid substitution sites | SEQ. ID NO. |
| --- | --- | --- |
| Alanine Substitutions | | |
| Ala1 | RS-R125 | 2 |
| Ala2 | QT130 | |
| Ala3 | ND133 | |
| Ala4 | E--N140 | |
| Ala4 + 5 | E--N140 + KEE146 | 3 |
| Ala5 | KEE146 | 15 |
| Ala6 | REK154 | 4 |
| Ala7 | EKY159 | 5 |
| Ala8 | Q-HN165 | 6 |
| Ala9 | N-DR172 | 7 |
| Ala10 | K--E179 | 16 |
| Ala13 | FQ118 | 8 |
| Ala14 | D120 | 9 |
| Leucine Substitutions | | |
| Leu | AAA136 | 10 |

The present methods utilize nucleic acid constructs encoding mutated versions of naturally occurring geminivirus AL1/C1 (Rep) proteins. The term "mutated" as used herein regarding proteins or polypeptides means that at least one amino acid in the wild-type or naturally occurring protein or polypeptide sequence has been replaced with a different amino acid, or deleted from the sequence. Preferably at least two or more adjacent amino acids in the wild-type sequence are replaced or deleted. Mutant AL1/C1 proteins may contain from about 2 to about 30, or more, replaced or deleted amino acids. A particularly preferred mutation is the replacement of conserved, charged or hydrophobic amino acid residues with alanine.

As used herein, the term "AL1/C1" or "Rep" protein refers to the geminivirus proteins that are known in the art as AL1/C1 proteins in geminiviruses. Subgroup II and III geminiviruses encode a protein that is identifiable by those skilled in the art, based on structure and/or function, as the AL1/C1 protein. As used herein, the term "AL1/C1" as it is applied to polypeptides includes fragments of AL1/C1 proteins. As used herein, the term "AL1/C1" as it is applied to nucleic acid sequences (including naturally occurring sequences and genes, and synthesized nucleic acid sequences) refers to sequences that encode a naturally occurring AL1/C1 protein or polypeptide, or a mutated AL1/C1 protein or peptide as described herein.

Mutated AL1/C1 proteins and polypeptides useful in the present methods are those which, when expressed in a plant cell, reduce the sensitivity of the cell (or a plant comprising such cells) to infection by a geminivirus. Mutated AL1/C1 proteins and polypeptides useful in the present methods are also those which, when expressed in a plant cell, increase or enhance the resistance or tolerance of the cell (or a plant comprising such cells) to infection by a geminivirus.

As used herein, "sensitivity" of a plant to infection by a geminivirus refers to the rate at which symptoms of geminivirus infection develop, and the severity of symptoms. Plants with reduced sensitivity to infection have delayed development of symptoms and/or less severe symptoms of geminivirus infection compared to that which occurs in a control plant.

As used herein, "tolerance" refers to plants that are infected with and contain a geminivirus, but do not show symptoms associated with viral infection. Tolerant crop plants are able to produce a good crop despite geminivirus infection. As used herein, plants that are "immune to infection" by a geminivirus are those in which replication of the virus is prevented. As used herein, plants that are "resistant" to infection by a geminivirus are those that show both immunity to infection and tolerance.

It will be apparent to those skilled in the art that the ability of a plant to survive and thrive when exposed to geminiviruses is a continuum, from plants that are less sensitive to infection, to those that are tolerant to infection, to those that are resistant to, geminiviruses. A plant that shows enhanced resistance or tolerance to geminivirus infection is considered herein to also show reduced sensitivity to geminivirus infection. In each case, the severity and/or rate of development of symptoms in plants with enhanced resistance (reduced sensitivity) to geminiviruses is less than that which occurs in a control plant.

Sensitivity, tolerance or resistance to geminivirus infection may be measured at the level of a plant cell or at the level of a single plant (e.g., by assessing the severity or rapidity of symptom development), or at the level of a plurality of plants (e.g., by assessing the prevalence and/or severity of infection, or the crop yield). Sensitivity in transgenic plants can be assessed by comparison to non-transformed control plants of the same species.

As used herein, the terms "protein" and "polypeptide" are used interchangeably, and refer to a polymer of amino acids (dipeptide or greater) linked through peptide bonds. Thus, the term "polypeptide" includes proteins, oligopeptides, protein fragments, protein analogs and the like. The term "polypeptide" contemplates polypeptides as defined above that are encoded by nucleic acids, are recombinantly produced, are isolated from an appropriate source, or are synthesized.

The mutated geminivirus AL1/C1 proteins useful in the present methods may be based on any naturally-occurring AL1/C1 protein. A series of site-directed mutants of any AL1/C1 protein can be prepared and screened for the ability to enhance geminivirus resistance (for example, using tobacco protoplast complementation assays as described in the Examples, below). Mutant AL1/C1 proteins or polypeptides capable of reducing sensitivity to geminivirus infection in transgenic plants according to the methods herein are identified, and nucleic acid constructs capable of encoding the mutant protein are prepared according to methods known in the art, for use in producing transgenic plants with reduced sensitivity to (or increased resistance or tolerance to) geminivirus infection.

As used herein, a "native" or "naturally-occurring" nucleic acid sequence is a sequence that is found in non-transgenic cells or tissue. Native nucleic acid sequences are thus those which have not been artificially altered, such as by site-directed mutagenesis. Once native nucleic acid sequences have been determined, molecules having these sequences can be synthesized or produced using recombinant nucleic acid procedures as are known in the art. As used herein, a native geminivirus nucleic acid sequence is that which can be isolated from a naturally-occurring geminivirus.

Mutants of AL1/C1 proteins from various geminiviruses are suitable for use in the present invention, including but not limited to: Tomato golden mosaic virus (TGMV), tomato mottle virus, tomato yellow leaf curl virus (TYLCV), tomato leaf curl virus (TLCV), potato yellow mosaic virus (PYMV), African cassava mosaic virus (ACMV), Indian cassava mosaic virus, bean golden mosaic virus (BGMV), bean dwarf mosaic virus, squash leaf curl virus, cotton leaf curl virus (CLCV), beet curly top virus (BCTV), Texas pepper virus and Pepper Huastico virus. A preferred mutant protein or polypeptide is one in which one or more amino acid residues are replaced with alanine.

The sequences of AL1/C1 proteins from various geminiviruses are known and available through GenBank.

Unless otherwise stated, nucleotide sequences are presented herein by single strand only, in the 5' to 3' direction, from left to right. Nucleotides are represented herein in the manner recommended by the IUPAC-IUB Biochemical Nomenclature Commission.

The methods and constructs of the present invention are useful in transforming dicot plant species to produce plants with reduced sensitivity to geminivirus infection. Dicots suitable for use in practicing the present invention include plants from the Fabaceae, Solanaceae, Brassicaceae, Rosaceae and Compositae families. Examples of plant species suitable for transformation with the DNA constructs of the present invention include but are not limited to tobacco (*Nicotiana tabacum*), potato (*Solanum tuberosum*), soybean (*glycine max*), tomato (*Lycopersicon esculentum*), cassava (*Manihot esculenta*), beets, peanuts (*Arachis hypogaea*), cotton (*Gossypium hirsutum*), citrus trees (*Citrus* spp.), corn or maize (*Zea mays*), beans (e.g., green beans (*Phaseolus vulgaris*) and lima beans (*Phaseolus limensis*)), peas (*Lathyrus spp.*), sugarbeet, sunflower, carrot, celery, flax, cabbage and other cruciferous plants, pepper, strawberry, lettuce, alfalfa, oat, wheat, rye, rice, barley, sorghum and canola. Thus an illustrative category of plants which may be transformed with the constructs of the present invention are members of the family Solanacae, and particular plants which may be transformed using the constructs of the present invention are tomato and tobacco.

A variety of techniques are available in the art for introduction of DNA constructs into a plant cell host. These include, but are not limited to, Agrobacterium-mediated transfection, injection, electroporation, microparticle bombardment. In preferred embodiments, plants are transfected using Agrobacterium-mediated transfection, or intact plants are inoculated using microprojectiles carrying a nucleic acid construct according to the present invention.

In practice, a crop comprising a plurality of plants of the invention may be planted together in an agricultural field. By "agricultural field" is meant a common plot of soil or a greenhouse. Thus, the present invention provides a method of providing a crop of transgenic plants.

Those familiar with recombinant DNA methods available in the art will recognize that one can employ a nucleic acid sequence coding for a mutant AL1/C1 protein of the present invention, joined in the sense orientation with appropriate operably linked regulatory sequences, to construct transgenic cells and plants. Appropriate regulatory sequences for expression of nucleic acid sequences in the sense orientation include any of the known eukaryotic translation start sequences, in addition to promoter and polyadenylation/transcription termination sequences.

Nucleic acid constructs (or "transcription cassettes") of the present invention include, 5' to 3' in the direction of transcription, a promoter as discussed above and, operatively associated with the promoter, a nucleic acid sequence encoding a mutant AL1/C1 protein of the present invention. The construct may optionally contain a termination sequence including stop signal for RNA polymerase. Each of these regulatory regions should be capable of operating in the cells of the tissue to be transformed. Any suitable termination signal may be employed in carrying out the present invention, examples thereof including, but not limited to, the nos terminator, the CaMV terminator, or native termination signals derived from the same gene as the transcriptional initiation region or derived from a different gene. The term "operatively associated," as used herein, refers to nucleic acid sequences on a single nucleic acid molecule, which sequences are associated so that the function of one is affected by the other. Thus, a promoter is operatively associated with a nucleic acid sequence when it is capable of affecting the transcription of that sequence (i.e., the sequence is under the transcriptional control of the promoter). The promoter is said to be "upstream" from the sequence, which is in turn said to be "downstream" from the promoter.

The various fragments comprising the various constructs, transcription cassettes, markers, and the like may be introduced consecutively by restriction enzyme cleavage of an appropriate replication system, and insertion of the particular construct or fragment into the available site. After ligation and cloning the nucleic acid construct may be isolated for further manipulation. All of these techniques are amply exemplified in the literature (see, e.g., J. Sambrook et al., Molecular Cloning, A Laboratory Manual (2d Ed. 1989) (Cold Spring Harbor Laboratory)).

The term "nucleic acid sequence" as used herein refers to a DNA or RNA molecule, and more particularly a linear series of deoxyribonucleotides or ribonucleotides connected to one another by bonds, typically phosphodiester bonds, between the 3' and 5' carbon of the adjacent pentoses.

The term "promoter" refers to a region of a DNA sequence that incorporates the necessary signals for the efficient expression of a coding sequence. This may include sequences to which an RNA polymerase binds but is not limited thereto, and may include other sequences to which other regulatory proteins bind, together with regions involved in the control of protein translation. Promoters employed in carrying out the present invention may be promoters that are constitutively active in the subject plant cell. Numerous constitutively active promoters which are operable in plants are available. A preferred example is the 35S promoter from fig wort mosaic virus (FMV), or the Cauliflower Mosaic Virus (CaMV) 35S promoter. In the alternative, the promoter may be promoter that is spatially active or active only in a specific tissue of the plant (see e.g., U.S. Pat. No. 5,459,252 for root-specific promoters), or an inducible promoter (e.g., a promoter active in plants that is induced by specific conditions, such as wounding or infection by specific pathogens).

Methods of making transgenic (or 'recombinant') plants of the present invention, in general, involve first providing a plant cell capable of regeneration (the plant cell typically residing in a tissue capable of regeneration). The plant cell is then transformed with a DNA construct comprising a transcription cassette of the present invention (as described herein) and a transgenic plant is regenerated from the transformed plant cell. The transforming step may be carried out by any suitable technique as is known in the art, including but not limited to bombarding the plant cell with microparticles carrying the transcription cassette, infecting the cell with an *Agrobacterium tumefaciens* containing a Ti plasmid carrying the transcription cassette, or any other suitable technique.

Vectors which may be used to transform plant tissue with the nucleic acid constructs of the present invention include both Agrobacterium vectors and ballistic vectors, as well as other suitable vectors known to those in the art. *Agrobac-* terium tumefaciens cells containing a nucleic acid construct of the present invention are useful in methods of making transformed plants. Plant cells are infected with an *Agrobacterium tumefaciens* to produce a transformed plant cell, and then a plant is regenerated from the transformed plant cell, according to methods known in the art. Numerous Agrobacterium vector systems useful in carrying out the present invention are known (see, e.g., U.S. Pat. Nos. 4,459,355; 4,795,855; 4,940,838).

Microparticles carrying constructs of the present invention, which microparticle is suitable for the ballistic transformation of a plant cell, are also useful for making transformed plants of the present invention. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050; in Christou et al., U.S. Pat. No. 5,015,58; and in Agracetus European Patent Application Publication No. 0 270 356, titled "Pollen-mediated Plant Transformation".

Plant species may be transformed with the nucleic acid constructs of the present invention by the DNA-mediated transformation of plant cell protoplasts and subsequent regeneration of the plant from the transformed protoplasts in accordance with procedures known in the art. Fusion of tobacco protoplasts with DNA-containing liposomes or via electroporation is known in the art (Shilleto et al., *Methods in Enzymology*, 153:313–336 (1987)).

As used herein, transformation refers to the introduction of exogenous nucleic acid molecules into cells, so as to produce transgenic cells stably transformed with the exogenous nucleic acid. Transformed plant cells are induced to regenerate intact plants through application of cell and tissue culture techniques that are known in the art. The method of plant regeneration is chosen so as to be compatible with the method of transformation. The stable presence and orientation of the exogenous DNA in transgenic plants can be verified by the Mendelian inheritance of the DNA sequence, as revealed by standard methods of DNA analysis applied to progeny resulting from controlled crosses.

Any plant tissue capable of subsequent clonal propagation, whether by organogenesis or embryogenesis, may be transformed with the constructs of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Transgenic plants of the present invention may take a variety of forms. The plants may be chimeras of transformed cells and non-transformed cells; the plants may be clonal transformants (e.g., all cells transformed to contain the transcription cassette); the plants may comprise grafts of transformed and non-transformed tissues. The transformed plants may be propagated by a variety of means known in the art, such as by clonal propagation or by classical breeding techniques.

The examples which follow are set forth to illustrate the present invention, and are not to be construed as limiting thereof.

EXAMPLE 1

Materials and Methods

Mutagenesis and Cloning of AL1 Proteins

The plasmid pNSB148 containing the AL1 coding sequence in a pUC 118-background, was used as the template for site directed mutagenesis. The oligonucleotide primers and resulting clones are listed in Table 4. DNA fragments containing the mutations were verified by DNA sequence analysis. Plant expression cassettes for mutant AL1 proteins were generated by subcloning SalI/NcoI fragments from the mutant clones into the same sites in a wild type AL1 plant expression cassette pMON1549 (Fontes et al., *Plant Cell* 6:405 (1994); Fontes et al., *J. Biol. Chem.* 269:8459 (1994)). In pMON1549, AL1 expression is under the control of the cauliflower mosaic virus 35S promoter with a duplicated enhancer region and the E9 3' end.

Baculovirus vectors were generated for expressing mutant and truncated AL1 proteins in insect cells. Expression vectors coding for mutant AL1 proteins were generated by subcloning BglII/BamHI inserts from the mutant plant expression cassettes into the BamHI site of pMON27025 (Luckow et al, *J. Virol.* 67:4566 (1993)). Expression vectors for the truncated proteins AL1 119–352 (pNSB516), AL1 1–120 (pNSB388), and AL1 1–180 (pNSB517) have been described previously. Orozco et al., *J. Biol. Chem.* 272:9840 (1997). N-terminal truncations, AL1 134–352 and AL1 147–352 were generated by inserting a DNA linker containing a start codon into the NotI site of pNSB593 and pNSB595. AL1 160–352 was created by inserting an SphI linker into the SspI site of pMON1539. SphI/BamHI fragments from the resulting clones were inserted into the same sites of the baculovirus vector, pNSB448, to give pNSB803 (AL1 134–352), pNSB876 (AL1 147–352) and pNSB633 (AL1 160–352). The C-terminal truncation AL1 1–158 (pNSB646) was created by digesting pMON1539 with NdeI and SspI, repairing with Klenow, and subcloning into the filled BamHI site of pMON27025. The AL1 1–168 truncation, pNSB708, was created by inserting an XbaI linker into the repaired BssHII of pNSB609.

TABLE 4

| Mutation | Oligonucleotide | Baculovirus Vector | Yeast GAL4-AD | Plant Expression |
|---|---|---|---|---|
| wt | N/A | pMON1680 | pNSB809 | pMON1549 |
| FQ118 (Ala13) | CACTTCGACCGTCGACCGCGGCTTCTCCCCA | N/A | pNSB872 | pNSB866 |
| D120 (Ala14) | CACTTCGGCCGGCGACCGCGGCTTCTCCCCA | N/A | pNSB871 | pNSB865 |
| RS-R125 (Ala1) | GCAACCTCCTgcAGCggccgcACCGTCGACCTGGA | N/A | pNSB786 | pNSB695 |

TABLE 4-continued

| Mutation | Oligonucleotide | Baculovirus Vector | Yeast GAL4-AD | Plant Expression |
|---|---|---|---|---|
| QT130 (Ala2) | CAGCGTCGTTgcaGcTgcGCAACCTCCTCTAGCA | N/A | pNSB788 | pNSB696 |
| ND133 (Ala3) | CTGCTGCAGCGgCcgcAGATGTTTGGCAA | pNSB603 | pNSB970 | pNSB670 |
| E--N140 (Ala4) | GGAAGAAGCAgcTAACGCggCcGCTGCAGCGTCGT | pNSB604 | ND | pNSB640 |
| KEE146 (Ala5) | TCTGCAGGGCTgCggCcgcGGAAGAAGCATTTAA | pNSB605 | ND | pNSB641 |
| REK154 (Ala6) | TTCTGGGATTgcggCcgcAATTATCTGCAGGG | pNSB605 | pNSB759 | pNSB671 |
| EKY159 (Ala7) | GAACTGAAATAAAgcggccgCTGGGATTTTCTCTC | pNSB607 | pNSB760 | pNSB672 |
| Q-HN165 (Ala8) | GCTATTTAGAgcGgcGAACgcAAATAAATATTTTTCTGGGAT | pNSB608 | pNSB761 | pNSB698 |
| N-DR172 (Ala9) | ATCAAATATCgcAgCTAgcgcGCTATTTAGATTGTG | pNSB609 | pNSB762 | pNSB707 |
| K--E179 (Ala10) | GAAGCCATGGcgCcGGAGTCgcATCAAATATCC | pNSB610 | pNSB763 | pNSB697 |
| AAA136 (Leu) | GAAGCAATTTAAgGCCTCTagTagAagGTCGTTAGATG | pNSB743 | pNSB785 | pNSB676 |
| E--N140 + KEE146 (Ala4 + 5) | TCTGCAGGGCTgCggCcgcGGAAGAAGCAgcTAACGCggCcGCTGCAGCGTCGT | pNSB659 | pNSB757 | pNSB648 |

Yeast expression cassettes were generated containing the coding sequence for AL1 fused to the Gal4 DNA binding domain, pNSB736, or Gal4 activation domain, pNSB809. The pAS2-1 Gal4 BD and Gal4 AD cloning vectors were purchased from Clontech. pNSB736- The BamHI/NdeI fragment of pMON1539 was cloned into the same sites of pAS2-1 pACT2-Gal4 AD vector to give pNSB736. pNSB735—the BamHI/Ndel fragment of pMon 1539 was cloned into the SmaI site of pACT2. pNSB809 replaced AatII/BamHI fragment from pNSB735 with the AatII/BamHI fragment from pMON1549. Mutant AL1 expression cassettes were created by replacing the AatII/BamHI wild type fragments from pNSB735 with AatII/BamHI inserts from the mutant plant expression cassettes.

Transient Replication Assays

Protoplasts were isolated from *Nicotiana tobacum* NT suspension cells, electroporated and cultured according to published methods (Fontes et al., *J. Biol. Chem.* 269:8459 (1994)). The transfections contained 15 µg each of replicon DNA containing a partial tandem copy of TGMV B (pTG1.4B described in Fontes et al., *Plant Cell,* 6:405 (1994)), wild type or mutant AL1 plant expression cassette and an AL3 plant expression cassette, (pNSB41 described in Fontes et al., *J. Biol. Chem.* 269:8459 (1994)).

Interference Assays

For the interference assays, transfections containing 2 µg of replicon DNA containing a partial tandem copy of TGMV A and 40 ug of mutant AL1 expression cassette or the empty expression vector. Total DNA was extracted 3 days post-transfection and analyzed for double- and single-stranded viral DNA accumulation by DNA gel blot hybridization.

Repression Assays

Protoplasts were isolated from *Nicotiana benthamiana* suspension cells, electroporated and cultured according to published methods (Eagle et al., *Plant Cell* 6:1157 (1994)).

AL1 Interactions in Yeast

The yeast strain Y187 was co-transformed with an expression cassette for wild type AL1 or maize Rb fused to the Gal4 binding domain (BD) and expression cassettes for mutant AL1 proteins fused to the Gal4 activation domain (AD). Total extracts were assayed for B-galactosidase activity using the substrate o-nitrophenyl B-D-galactopyranoside, essentially as described by Clontech (Palo Alto, Calif.). Protein concentrations were measured by Bradford assays. The activities were standardized against wild type AL1 fused to both the Gal4 activation domain and DNA binding domain.

EXAMPLE 2

Limits of the AL1 Oligomerization Domain

The domains for TGMV AL1 DNA binding and DNA cleavage/ligation activity have been well defined and key structural and sequence motifs have been identified for these activities. Orozco et al., *J. Biol. Chem.* 273:24448 (1998). In contrast, TGMV AL1 protein interactions with the viral protein AL3, plant retinoblastoma (Rb) homologue, and AL1 itself have been broadly mapped to overlapping domains in the center of the protein. In the present studies, additional N- and C-terminal truncations were generated to further define the limits of the AL1 oligomerization domain (FIG. 2A). Full length GST-AL1 1–352 was coexpressed with truncated AL 1 proteins in baculovirus-infected insect cells and purified on glutathione-sepharose resin. Total extracts and purified proteins were resolved by SDS-PAGE and AL1 was visualized by immunoblotting with AL1 polyclonal antisera. As reported previously, the C-terminal truncation AL1 1–180 (FIG. 2B, lanes 3 and 6) co-purified with full length GST-AL1 1–352. Further deletion of the C-terminus to amino acids 168 (lanes 2 and 5) and 158 (lanes 1 and 4) abolished interactions with GST-AL1 protein, demonstrating that the C-terminal limits of the oligomerization domain are between positions 168 and 180. In contrast, N-terminal truncation mutations AL1 134–352 (FIG. 2C, lanes 3 and 6), AL1 147–352 (lanes 2 and 5) and AL1 160–352 (lanes 1 and 4) showed a gradual disappearance of interactions with GST-AL1 1–352; the AL1 147–352 and AL1 160–352 interactions varied between weak to background levels. Thus, the N-terminal limit of the oligomerization domain was more difficult to define.

Authentic (i.e., native or natural) AL1 also co-purified with a 60 amino-acid fragment of AL1 fused to GST (GST-AL1 119–180 but not with GST alone (FIG. 4A, lanes 1 and 2), demonstrating that sequences between amino acids 119 and 180 are sufficient for AL1 oligomerization. However, additional amino acid contacts may contribute to dimer stability or multimerization. Interactions between GST-AL1 119–180 and the N-terminal truncations of AL1 were then tested. In this assay, deletion to positions 119 (FIG. 2D, lanes 1 and 5) and 134 (lanes 2 and 6) did not affect oligomerization, whereas further deletion to positions 147 (lanes 3 and 7) and 160 (lanes 4 and 8) abolished interactions with GST-AL1 119–180.

Together, the results showed that AL1 amino acids 134 to 180 contain the core oligomerization domain and indicated that sequences outside the core contribute additional contacts.

EXAMPLE 3

Mutations in the Oligomerization Domain Affect AL1 Complex Stability.

Alanine substitutions were generated in conserved and charged residues within the core oligomerization domain and adjacent sequences to identify key amino acids that contribute to AL1 interactions (FIG. 3). Wild type AL1 and proteins with mutations in the core oligomerization domain (E—N140 (Ala4), KEE146 (Ala5), REK154 (Ala6), EKY159 (Ala7), Q-HN165 (Ala8), N-DR172 (Ala9) and K—E179 (Ala10) were expressed with full length GST-AL1 in insect cells (FIG. 4A, top panel) and co-purified on glutathione resin (FIG. 4A, bottom panel). Wild-type (lane 1) and mutant AL1 proteins (lanes 3–9) all interacted with GST-AL1. Wild type AL1 did not co-purify with GST alone (lane 2), demonstrating that the interactions were specific for AL1. Similar experiments using GST-AL1 119–180 (FIG. 4B) identified one mutant EKY159 (Ala7, lane 6), defective for AL1 interactions. Thus a mutation that impaired AL1 oligomerization was revealed only when co-purified with the core oligomerization domain alone, consistent with the observation that sequences outside the domain contribute to stabilizing interactions.

AL1 EKY159 was assayed for co-purification with truncated GST-AL1 proteins to identify the region that stabilized interactions with the mutant protein. As described above, AL1 EKY159 interacted with full length GST AL1 (FIG. 4C, lanes 1 and 5) but not with GST-AL1(119–180) (lanes 4 and 8). AL1 EKY159 interacted with an N-terminal truncation of AL1, GST-AL1(119–352) (lanes 3 and 7) whereas no interaction was detected with a C-terminal truncation of AL1, GST-AL1(1–180) (lanes 2 and 6). These results demonstrate that the C-terminus contributes additional protein contacts outside of the oligomerization domain that can mask the effect of oligomerization mutations within the core domain.

The co-purification assay in insect cells established the limits of the AL1 oligomerization domain and identified amino acids that may be required for protein interactions. The quantitative impact of the mutations on AL1 oligomerization was then analyzed by yeast two-hybrid assays. Expression cassettes for AL1 fused to the GAL4 DNA binding domain and wild type or mutant AL1 fused to the GAL4 activation domain were co-transformed into yeast. Activation of the promoter was assayed by measuring the beta-galactosidase activity in total yeast extracts. Interactions between the mutant and wild type AL1 fusion proteins were then expressed as a percent of wild type AL1/AL1 mediated activation (FIG. 5A). Four of the mutations reduced AL1 interactions to 51% (KEE146, Ala5), 57% (REK154, Ala6), 0% (EKY159, Ala7), and 31% (N-DR172, Ala9) of wild type. In contrast, the mutation Q-HN165 (Ala8) and K-E179 (Ala10) interactions were comparable to wild type. These mutations, located between amino acids 143 and 172, are within the core oligomerization domain. Mutations N-terminal to the core domain, D120 (Ala14), QT130 (Ala2), ND133 (Ala3), and E-N140 (Ala4) were less impaired for AL1 oligomerization, consistent with a role in providing stabilizing contacts to the interaction. The mutation FQ118 (Ala 13) showed no impact on AL1 interactions. Although the mutation RS-R125 (Ala1) is located outside the core domain, AL1 interactions were reduced to 27% of wild type. However, this protein is also impaired for DNA binding. Mutant proteins with reduced AL1 interactions in yeast, REK154 (Ala6), EKY159 (Ala7) and N-DR172 (Ala9) were expressed at levels comparable to wild type, as determined by immunoblot of total protein extracts. Thus, the reduced interactions were not attributable to reduced protein expression levels.

The impact of the AL1 mutations on binding to maize Rb was also analyzed by yeast two-hybrid assays. Expression cassettes for maize Rb (amino acids 214–866) fused to the GAL4 DNA binding domain and mutant AL1 proteins fused to the GAL4 activation domain were co-transformed into yeast. Activation of the promoter was assayed by measuring the beta-galactosidase activity in total yeast extracts. Results were then expressed as a percent of wild type AL1/Rb mediated activation (FIG. 5B).

Earlier studies have shown that TGMV AL1 and Rb interact with each other, but the region of the AL1 protein that mediates interaction was not known. The limits of the Rb binding domain were defined by the present inventors using a baculovirus expression system. Insect cells were co-infected with recombinant baculoviruses corresponding to various AL1 truncations and to a GST fusion with amino acids 214–866 of Maize Rb (GST-mRb). The abilities of the different AL1truncation to bind GST-mRb were assessed by cofractionation on glutathione-sepharose resin. Total extracts and purified proteins were resolved by SDS-PAGE, and AL1 and GST-mRb were visualized by immunoblotting with AL1 and GST antibodies, respectively. The C-terminal truncation AL1(1–180) copurified with GST-mRb. Further deletion to amino acids 168 and 158 abolished interactions with GST-mRb. Similarly, the N-terminal truncation AL1 (101–352) cofractionated with GST-mRb, whereas truncations at positions 110 and 119 were unable to bind GST-mRb. Together, these results mapped the limits of pRB binding domain between AL1 amino acids 101 and 180. Thus, the C-termini of the pRb binding and oligomerization domains of TGMV AL1 are contiguous, whereas an additional 33 N-terminal amino acids are required for Rb binding (data not shown).

Seven mutants displayed reduced Rb binding activity. These mutants fell into two distinct classes. One group, which included the core oligomerization domain mutants REK154 (Ala6), EKY159 (Ala7), N-DR172 (Ala9), was impaired to similar degrees for Rb binding and AL1 oligomerization, suggesting that AL1/AL1 interactions may be a prerequisite for binding to Rb. The second group were more severely impaired for Rb binding than for AL1 oligomerization and thus most likely reflect specific AL1 amino acids that contact Rb. This group included FQ118 (Ala13), RS-R125 (Ala1), AAA136 (Leu), KEE146 (Ala5). One mutant, Q-HN165 (Ala8) displayed enhanced Rb binding activity.

EXAMPLE 4

AL1 Mutants in the Oligomerization Domain Impair Viral DNA Replication

The mutations were also assayed for their effect on AL1 functions in vivo. Plant expression cassettes for wild type and mutant AL1 were transfected into NT-1 protoplasts with TGMV B DNA and an expression cassette for AL3. Eleven of the twelve mutants were impaired for the ability to direct viral DNA replication (FIG. 6A) when compared to wild type AL1 (lane 1). Only the mutant, AL1 K—E179 (Ala10) supported wild type replication levels (lane 13). Mutations within the core oligomerization domain (lanes 9–12) and the conserved sequence between amino acids 117 and 125 (lanes 2–4) abolished replication. The latter group of mutations are within the DNA cleavage and DNA binding domains as well as the enhancer region for AL1 oligomerization and may have pleiotropic effects on AL1 activity. For example, AL1RS-R125 is impaired for DNA binding (results not shown) as well as AL1 oligomerization. In contrast, low levels of DNA synthesis were observed with AL1 mutations in the predicted alpha-helices (lanes 5–8), suggesting that the sequence of this region is less critical for AL1 function.

EXAMPLE 5

AL1 Mutants Interfere with Normal Viral DNA Replication

Whether replication defective AL1 could interfere with normal viral DNA replication was studied. The present inventors tested N-terminal and C-terminal truncations of wild type AL1, which lack the domains for one or more AL1 activities, and an N-terminal truncation of the AL1 N-DR172 mutant for dominant negative interference of viral replication. The oligomerization domain fused to GST (FIG. 7B) and a C-terminal truncation of AL1(1–181) (lane 3) reduced wild type replication, but were significantly less effective than the full length mutant proteins (FIG. 7A). In addition, replication interference by the N-DR172 mutant was less severe in the N-terminal truncated protein (FIG. 7B, lane 4) than in the full length AL1

A wild type TGMV A replicon (2 μg) was transfected into NT-1 protoplasts in the absence and presence of 20-fold excess (40 μg) mutant AL1 expression cassettes. Total DNA was isolated three days post-transfection and analyzed by DNA gel blot hybridization using a radiolabelled TGMV A probe. Mutations in the core oligomerization domain (FIG. 7A), REK154 (Ala6, lane 5), EKY159 (Ala7, lane 6), Q-HN165 (Ala8, lane 7), and N-DR172 (Ala9, lane 8) reduced single-stranded DNA accumulation 5 to 25% of wild type, and double-stranded DNA accumulation 8 to 29%.

Mutations outside the oligomerization domain, FQ118 (Ala13, lane 2) and D120 (Ala14, lane3), also interfered with replication, reducing single stranded DNA to 3 and 5% of wild type, and double stranded DNA to 1% to 6%, respectively. The mutation RS-R125 (Ala1, lane 4) was the least detrimental, reducing single and double stranded DNA by about 50%.

AL1 proteins defective for viral DNA replication interfered with TGMV A DNA replication. These results demonstrate that AL1 mutations that impair replication in vivo and affect oligomerization in vitro are good candidates for developing transgenic plants resistant to geminivirus infection.

EXAMPLE 6

Mutations in Conserved Amino Acids that Attenuate Viral DNA Replication also Enhance Repression of the AL1 Promoter The ability of the mutants to repress AL1 promoter activity in vivo was studied. The AL1 promoter fused to the luciferase reporter gene (lux) was transfected into *N. benthamiana* protoplasts either alone or in the presence of plant expression cassettes for wild type and mutant AL1 proteins, in these experiments, wild type AL1 repressed transcription from the AL1 promoter approximately 20-fold. Repression mediated by mutant AL1 proteins was standardized to the percent of wild type repression within each experiment. All of the mutants that reduced viral DNA replication (except for Ala1), also repressed promoter activity 2- to 4-fold higher than wild type AL1. DNA binding is required for repression and Ala1 is a DNA binding mutant. AL1 K—E179 (Ala10) supported normal replication levels and repressed the AL1 promoter similar to wild type AL1. FIG. 6A (see lane 13) and FIG. 6B.

What is claimed is:

1. An isolated nucleic acid comprising a nucleotide sequence encoding an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

2. A vector comprising the nucleic acid of claim 1.

3. A method of making a transgenic plant having increased resistance to geminivirus infection, comprising:
   a) introducing the nucleic acid of claim 1 into a plant cell capable of regeneration; and
   b) regenerating a transgenic plant from said plant cell, wherein expression of said nucleic acid increases resistance of said plant to infection by at least one geminivirus, compared to a control plant.

4. A method of making a transgenic plant having increased resistance to geminivirus infection, comprising:
   a) introducing the vector of claim 2 into a plant cell capable of regeneration; and
   b) regenerating a transgenic plant from said plant cell, wherein expression of said nucleic acid increases resistance of said plant to infection by at least one geminivirus, compared to a control plant.

* * * * *